US007829097B2

(12) United States Patent
Tsung et al.

(10) Patent No.: US 7,829,097 B2
(45) Date of Patent: Nov. 9, 2010

(54) USE OF HMGB1 FOR PROTECTION AGAINST ISCHEMIA REPERFUSION INJURY

(75) Inventors: Allan Tsung, Pittsburgh, PA (US); Timothy R. Billiar, Presto, PA (US); Mitchell P. Fink, Pittsburgh, PA (US); Kevin J. Tracey, Old Greenwich, CT (US)

(73) Assignees: University of Pittsburgh - Of the Commonwealth System of Higher Education, Pittsburgh, PA (US); The Feinstein Institute for Medical Research, Manhasset, NY (US)

( * ) Notice: Subject to any disclaimer, the term of this patent is extended or adjusted under 35 U.S.C. 154(b) by 454 days.

(21) Appl. No.: 11/671,932

(22) Filed: Feb. 6, 2007

(65) Prior Publication Data

US 2008/0004207 A1   Jan. 3, 2008

Related U.S. Application Data

(60) Provisional application No. 60/765,545, filed on Feb. 6, 2006.

(51) Int. Cl.
*A61K 38/18* (2006.01)
(52) U.S. Cl. .................................. 424/185.1
(58) Field of Classification Search ........................ None
See application file for complete search history.

(56) References Cited

U.S. PATENT DOCUMENTS

| | | | |
|---|---|---|---|
| 4,485,045 | A | 11/1984 | Regen |
| 4,544,545 | A | 10/1985 | Ryan et al. |
| 4,554,101 | A | 11/1985 | Hopp |
| 5,013,556 | A | 5/1991 | Woodle et al. |
| 6,811,768 | B2 | 11/2004 | Zapol et al. |
| 2003/0060410 | A1 | 3/2003 | Tracey et al. |
| 2004/0136979 | A1 | 7/2004 | Bianchi et al. |
| 2007/0154529 | A1 | 7/2007 | Bullerdiek |

FOREIGN PATENT DOCUMENTS

| | | |
|---|---|---|
| WO | WO 00/47104 A2 | 8/2000 |
| WO | WO 03/026691 A2 | 4/2003 |
| WO | WO 2004/004763 A2 | 1/2004 |
| WO | WO 2004/061456 A2 | 7/2004 |

OTHER PUBLICATIONS

Tsung et al., J. Immunol. 2005;175;7661-7668.*
Racanelli et al., Hepatology. Feb. 2006;43(2 Suppl 1):S54-62.*
Teoh et al., Hepatology. Jan. 2003;37(1):118-28.*
Ueta et al., The Journal of Immunology, 2004, 173: 3337-3347.*
Uronen-Hansson et al., Immunology. Feb. 2004;111(2):173-8.*
Guillot et al., J Biol Chem. Jan. 23, 2004;279(4):2712-8.*
Hornef et al., J Exp Med. Mar. 4, 2002;195(5):559-70.*
Kokkola et al., Scand J Immunol. Jan. 2005;61(1):1-9.*
Park et al., J Biol Chem. Feb. 27, 2004;279(9):7370-7.*
Watanabe et al., Journal of Surgical Research 124, 59-66 (2005).*
Muller et al., Journal of Internal Medicine 2004; 255: 332-343.*
Ronfani et al., Development 128, 1265-1273 (2001).*
Tanaka et al., Pediatr Transplant. Feb. 2005;9(1):47-51.*
Zaroff et al., Circulation. Aug. 13, 2002;106(7):836-41.*
Abraham et al., "Cutting Edge: HMG-1 as a Mediator of Acute Lung Inflammation," *The Journal of Immunology*, 165(6): 2950-2954 (Sep. 15, 2000).
Andersson et al., "High Mobility Group 1 Protein (HMG-1) Stimulates Proinflammatory Cytokine Synthesis in Human Monocytes," *J. Exp. Med.* 192(4): 565-570 (Aug. 21, 2000).
Bianchi et al., "the DNA Binding Site of HMG1 Protein is Composed of Two Similar Segments (HMG Boxes), Both of Which Have Counterparts in Other Eukaryotic Regulatory Proteins," *The EMBO Journal* 11(3): 1055-1063 (Mar. 1992).
Cavalieri et al., "Ischemic Preconditioning Attenuates the Oxidant-Dependent Mechanisms of Reperfusion Cell Damage and Death in Rat Liver," *Liver Transplantation*, 8(11): 990-999 (Nov. 2002).
Colletti et al., "LPS Pretreatment Protects form Hepatic Ischemia/Reperfusion," *Journal of Surgical Research* 57(3): 337-343 (Sep. 1994).
Elhage et al., "Differential Effects of Interleukin-! Receptor Antagonist and Tumor Necrosis Factor Binding Protein on Fatty-Streak Formation in Apolipoprotein E-Deficient Mice," *Circulation*, 97(3): 242-244 (Jan. 27, 1998).
Epstein et al., "Biological Activity of Liposome-Encapsulated Murine Interferon Y is Mediated by a Cell Membrane Receptor," *Proceedings of the National Academy of Sciences USA*, 82(11): 3688-3692 (Jun. 1985).
Hwang et al., "Hepatic Uptake and Degradation of Unilamellar Sphingomyelin/Cholesterol Liposomes: A Kinetic Study," *Proceedings of the National Academy of Sciences USA*, 77(7): 4030-4034 (Jul. 1980).
Ishikawa et al., "Heat Shock Preconditioning on Mitochondria During Warm Ischemia in Rat Livers," *Journal of Surgical Research*, 87(2): 178-184 (Dec. 1999).
Kyte et al., "A Simple Method for Displaying the Hydropathic Character of a Protein," *Journal of Molecular Biology*, 157(1): 105-115 (May 5, 1982).
Li et al., "Structural Basis for the Proinflammatory Cytokine Activity of High Mobility Group Box 1," *Molecular Medicine*, 37-45 (Jan./Feb. 2003).
Martin et al., "Irreversible Coupling of Immunoglobulin Fragments to Preformed Vesicles," *The Journal of Biological Chemistry*, 257(1): 286-288 (Jan. 10, 1982).
Murry et al., "Preconditioning with Ischemia: A Delay of Lethal Cell Injury in Ischemic Myocardium," *Circulation*, 74(5): 1124-1136 (Nov. 1986).
NCBI, "HMG-1," Database Entrez-Protein, Accession No. AAA20508 (Aug. 5, 1994). Retrieved on Feb. 14, 2007.
NCBI, "Non-Histone Protein HMG1," Database Entrez-Protein, Accession No. AAA31050 (Apr. 27, 1993). Retrieved on Feb. 14, 2007.
NCBI, "Amphoterin," Database Entrez-Protein, Accession No. AAA40729 (Apr. 27, 1993). Retrieved on Feb. 14, 2007.

(Continued)

*Primary Examiner*—Zachary Skelding
(74) *Attorney, Agent, or Firm*—Leydig, Voit & Mayer, Ltd.

(57) ABSTRACT

Methods and compositions are disclosed for protecting an organ or tissue from inflammation and organ injury following ischemia, reperfusion, and trauma through the administration of an HMGB1 protein within a time period sufficient to protect the organ or tissue from injury.

30 Claims, 5 Drawing Sheets

OTHER PUBLICATIONS

Figure 1A:
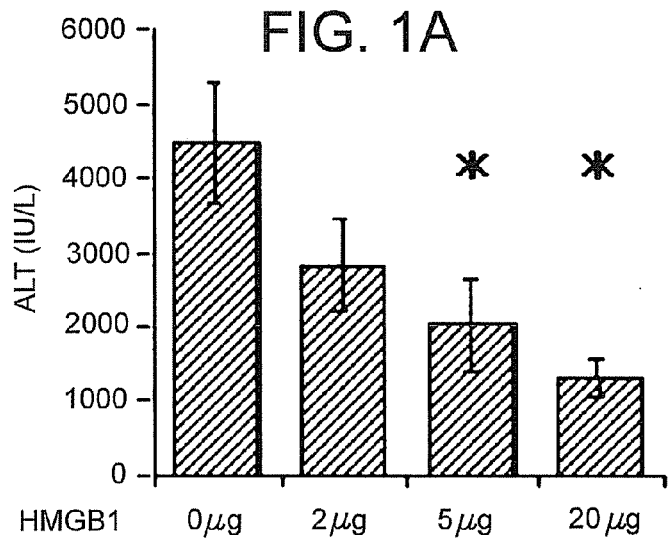

NCBI, "HMG-1," Database Entrez-Protein, Accession No. AAA64970 (Apr. 11, 1995). Retrieved on Feb. 14, 2007.
NCBI, "Non-Histone Chromatin Protein HMG1 [Homo Sapiens]," Database Entrez-Protein, Accession No. AAB08987 (Sep. 27, 1996). Retrieved on Feb. 14, 2007.
NCBI, "High Mobility Group Protein [Spalax Ehrenbergi]," Database Entrez-Protein, Accession No. AAC27651 (Jul. 28, 1998). Retrieved on Feb. 14, 2007.
NCBI, "Hypothetical Protein MGC75695 [Xenopus Tropicalis]," Database Entrez-Protein, Accession No. AAH63332 (Jul. 15, 2006). Retrieved on Feb. 14, 2007.
NCBI, "High Mobility Group Box 1 [Rattus Norvegicus]," Database Entrez-Protein, Accession No. AAH88402 (Dec. 2, 2006). Retrieved on Feb. 14, 2007.
NCBI, "HMGB! Protein [Bos Taurus]," Database Entrez-Protein, Accession No. AAI02930 (Jan. 23, 2007). Retrieved on Feb. 14, 2007.
NCBI, "Homo Sapiens High-Mobility Group Box 1 [Synthetic Contruct]," Database Entrez-Protein, Accession No. AAP36330 (May 13, 2003). Retrieved on Feb. 14, 2007.
NCBI, "High-Mobility Group Box 1 [Homo Sapiens]," Database Entrez-Protein, Accession No. AAV38961 (Oct. 28, 2004). Retrieved on Feb. 14, 2007.
NCBI, "High Mobility Group 1 Protein [Gallus Gallus]," Database Entrez-Protein, Accession No. CAA76978 (Apr. 18, 2005). Retrieved on Feb. 14, 2007.
NCBI, "HMGB1 [Homo Sapiens]," Database Entrez-Protein, Accession No. CAG33144 (Apr. 17, 2005). Retrieved on Feb. 14, 2007.
NCBI, "High-Mobility Group Box 1 [Homo Sapiens]," Database Entrez-Protein, Accession No. NP_002119 (Feb. 4, 2007). Retrieved on Feb. 14, 2007.
NCBI, "High Mobility Group Protein 1 (HMG-1) (Amphoterin) (Heparin-binding protein p30)," Database Entrez-Protein, Accession No. P07155 (Oct. 1, 2004). Retrieved on Feb. 14, 2007.
NCBI, "High Mobility Group Protein B1 (High Mobility Group Protein 1) (HMG-1)," Database Entrez-Protein, Accession No. P09429 (Jan. 23, 2007). Retrieved on Feb. 14, 2007.
NCBI, "Nonhistone Chromosomal Protein HMG-1—Human," Database Entrez-Protein, Accession No. S29857 (Jul. 23, 1999). Retrieved on Feb. 14, 2007.
NCBI, "Predicted: Similar to High Mobility Group Protein 1 (HMG-1) (High Mobility Group Protein B1) (Amphoterin) (Heparin-Binding Protein p30) Isoform 1 [Mus Musculus]," Database Entrez-Protein, Accession No. XP_484795 (Jan. 11, 2006). Retrieved on Feb. 14, 2007.
NCBI, "Predicted: Similar to High Mobility Group Box 1; High Mobility Group Protein 1 [Pan Troglodytes]," Database Entrez-Protein, Accession No. XP_516325 (Nov. 9, 2004).
Shohami et al., "Cytokine Production in the Brain Following Closed Head Injury: Dexanabinlo (HU-211) is a Novel TNF-α Inhibitor and an Effective Neuroprotectant," *Journal of Neuroimmunology*, 72(2): 169-177 (Feb. 1997).
Terregino et al. "Endogenous Mediators in Emergency Department Patients With Presumed Sepsis: Are Levels Associated With Progression to Severe Sepsis and Death," *Annals of Emergency Medicine*, 35(1): 26-34 (Jan. 2000).
Tsai et al., "Preconditioning: Evolution of Basic Mechanisms to Potential Therapeutic Strategies," *Shock*, 21(3): 195-209 (Mar. 2004).
Tsung et al., "The Nuclear Factor HMGB1 Mediates Hepatic Injury After Murine Liver Ischemia-Reperfusion," *The Journal of Experimental Medicine*, 201(7): 1135-1143 (Apr. 4, 2005).
Wang et al., "HMG-1 as a Late Mediator of Endotoxin Lethality in Mice," *Science*, 285: 248-251 (Jul. 9, 1999).
Yang et al., "Reversing Established Sepsis with Antagonists of Endogenous High-Mobility Group Box 1," *Proceedings of the National Academy of Sciences USA* 101(1): 296-301 (Jan. 6, 2004).
International Search Report dated Mar. 3, 2008, in PCT/US2007/061709.

Written Opinion of International Search Report dated Mar. 3, 2008, in PCT/US2007/061709.
Akira et al., "Toll-Like Receptor Signalling," *Nature Reviews Immunology*, 4: 499-511 (Jul. 2004).
Aneja et al., "Preconditioning With High Mobility Group Box 1 (HMGB1) Induces Lipopolysaccharide (LPS) Tolerance," *Journal of Leukocyte Biology*, 84: 1326-1334 (Nov. 2008).
Arumugam et al., "Toll-Like Receptors in Ischemia-Reperfusion Injury," *Shock*, 32(1): 4-16 (Jul. 2009).
Cao et al., "IRAK: A Kinase Associate with the Interleukin-1 Receptor," *Science*, 271(5252): 1128-1131 (Feb. 23, 1996).
Colletti et al., "The Role of Cytokine Networks in the Local Liver Injury Following Hepatic Ischemia/Reperfusion in the Rat," *Hepatology*, 23(3): 506-514 (Mar. 1996).
Degryse et al., "The High Mobility Group (HMG) Boxes of the Nuclear Protein HMG1 Induce Chemotaxis and Cytoskeleton Reorganization in Rat Smooth Muscle Cells," *The Journal of Cell Biology*, 152(6): 1197-1206 (Mar. 19, 2001).
Fondevila et al., "Hepatic Ischemia/Reperfusion Injury—A Fresh Look," *Experimental and Molecular Pathology*, 74: 86-93 (2003).
Hatano et al., "NF-KB Stimulates Inducible Nitric Oxide Synthase to Protect Mouse Hepatocytes From TNF-α-and Fas-Mediated Apoptosis," *Gastroenterology*, 120(5): 1251-1262 (Apr. 2001).
Hu et al., "Preconditioning With High Mobility Group Box 1 Protein Protects Against Myocardial Ischemia-Reperfusion Injury," *International Journal of Cardiology*, (2009).
Iimuro et al., "NF$_K$B Prevents Apoptosis and Liver Dysfunction during Liver Regneration," *J. Clin. Invest.*, 101(4): 802-811 (Feb. 1998).
Johnson et al., "Receptor-Mediated Monitoring of Tissue Well-Being Via Detection of Soluble Heparan Sulfate by Toll-Like Receptor 4," *The Journal of Immunology*, 168: 5233-5239 (2002).
Klune et al., "HMGB1 Preconditioning: Therapeutic Application for a Danger Signal?" *Journal of Leukocyte Biology*, 83: 558-563 (Mar. 2008).
Kobayashi et al., IRAK-M Is a Negative Regulator of Toll-like Receptor Signaling, *Cell*, 110: 191-202 (Jul. 26, 2002).
Liu et al., "HMGB1 is Secreted by Immunostimulated Enterocytes and Contributes to Cytomix-Induced Hyperpermeability of Caco-2 Monolayers," *Am. J. Physiol. Cell Physiol.* 290(4): C990-C999 (Apr. 2006).
McCallion et al., "Ischemic Preconditioning Ameliorates Ischemia- and Reperfusion-Induced Intestinal Epithelial Hyperpermeability in Rats," *Shock*, 14(4): 429-434 (Oct. 2000).
Park et al., "Involvement of Toll-like Receptors 2 and 4 in Cellular Activation by High Mobility Group Box 1 Protein," *The Journal of Biological Chemistry*, 279(9): 7370-7377 (Feb. 27, 2004).
Park et al., High Mobility Group Box-1 Protein (HMGB1) Interacts with Multiple Toll Like Receptors, *Am. J. Physiol Cell Physiol.*, 290(3): C917-C924 (Mar. 2006).
Scaffidi et al., "Release of Chromatin Protein HMGB1 by Necrotic Cells Triggers Inflammation," *Nature*, 418: 191-195 (Jul. 11, 2002).
Selzner et al., "Protection Strategies Against Ischemic Injury of the Liver," *Gastroenterology*, 125(3): 917-936 (Sep. 2003).
Smiley et al., "Fibrinogen Stimulates Macrophage Chemokine Secretion Through Toll-Like Receptor 4," *The Journal of Immunology*, 167: 2887-2894 (2001).
Takahashi et al., "Role of NF-$_K$B on Liver Cold Ischemia-Reperfusion Injury," *Am. J. Physiol. Gastrointest. Liver Physiol.*, 283: G1175-G1184 (Nov. 2002).
Termeer et al., "Oligosaccharides of Hyaluronan Activate Dendritic Cells via Toll-like Receptor 4," *J. Exp. Med.* 195(1): 99-111 (Jan. 7, 2002).
Vabulas et al., "HSP70 as Endogenous Stimulus of the Toll/Interleukin-1 Receptor Signal Pathway," *The Journal of Biological Chemistry*, 277(17): 15107-15112 (Apr. 26, 2002).
Wanner et al., "Differential Effect of Anti-TNF-α Antibody on Proinflammatory Cytokine Release by Kupffer Cells Following Liver Ischemia and Reperfusion," *Shock*, 11(6): 391-395 (Jun. 1999).

Yoshidome et al., "Interleukin-10 Suppresses Hepatic Ischemia/Reperfusion Injury in Mice: Implications of a Central Role for Nuclear Factor $_K$B," *Hepatology*, 30(1): 203-208 (Jul. 1999).

Yotov et al., "Nucleotide Sequence of a Mouse cDNA Encoding the Non-Histone Chromosomal High Mobility Group Protein-1 (HMG1)," *Nucleic Acids Research*, 20(13): 3516 (1992).

Zhai et al., "Cutting Edge: TLR4 Activation Mediates Liver Ischemia/Reperfusion Inflammatory Response via IFN Regulatory Factor 3-Dependent MyD88-Independent Pathway," *The Journal of Immunology*, 173: 7115-7119 (2004).

\* cited by examiner

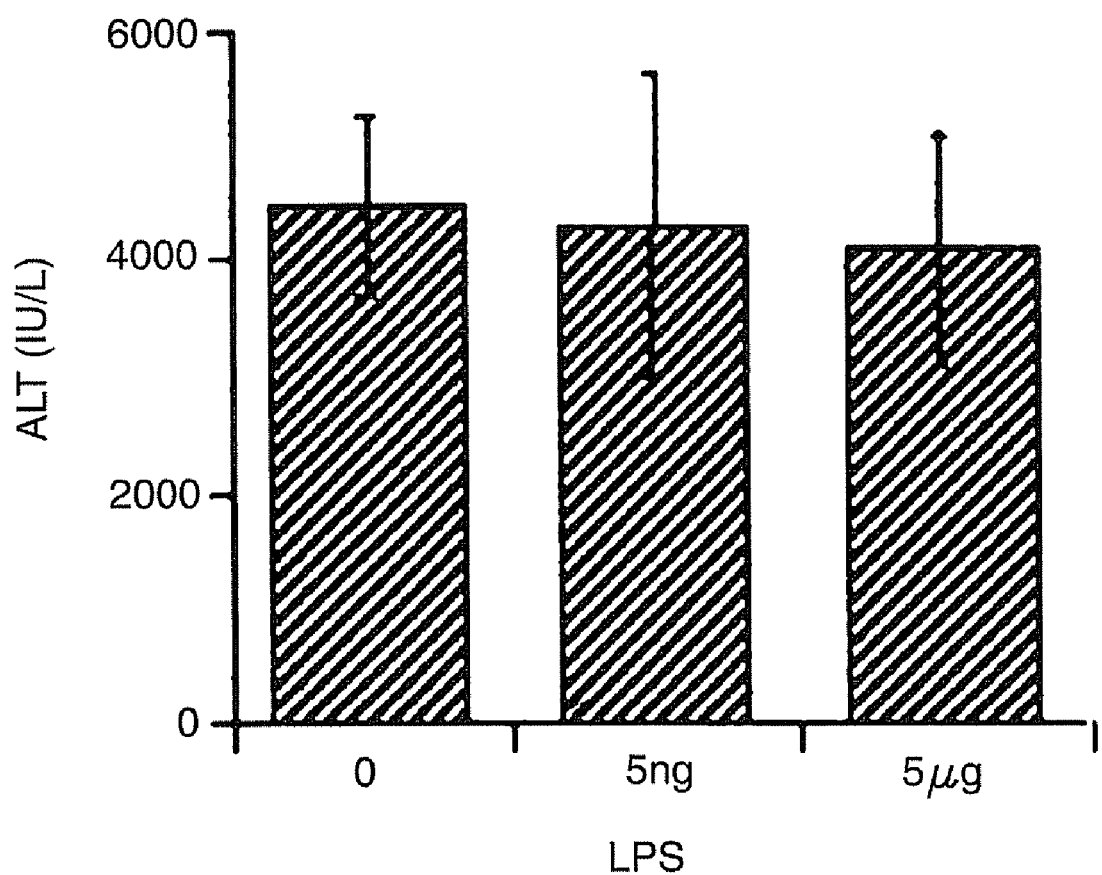

USE OF HMGB1 FOR PROTECTION AGAINST ISCHEMIA REPERFUSION INJURY

CROSS-REFERENCE TO RELATED APPLICATIONS

This patent application claims the benefit of U.S. Provisional Patent Application No. 60/765,545 filed Feb. 6, 2006, which is incorporated by reference in its entirety herein.

STATEMENT REGARDING FEDERALLY SPONSORED RESEARCH AND DEVELOPMENT

This invention was made in part with government support under Grant Numbers R01-GM50441, R01-GM37631, R01-GM-53789, R01-GM52021, and P50-GM53789 awarded by the National Institutes of Health. The government has certain rights in the invention.

SEQUENCE LISTING

Incorporated by reference in its entirety herein is a computer-readable nucleotide/amino acid sequence listing submitted concurrently herewith and identified as follows: One 36,000 Byte ASCII (Text) file named "256582ST25.TXT," created on Feb. 5, 2007.

BACKGROUND OF THE INVENTION

Inflammation is the reaction of living tissue to injury. During inflammation, a complex of cytologic and chemical reactions of affected blood vessels and adjacent tissues respond to an injury or abnormal stimulation caused by a physical, chemical or biological agent. Signaling agents are released, attracting tissue macrophages and white blood cells. Proinflammatory cytokines such as tumor necrosis factor (TNF) and interleukin-1 (IL-1) are activated, giving rise to inflammation.

Proinflammatory cytokines such as TNF and IL-1 are mediators of septic shock and associated cardiopulmonary dysfunction, acute respiratory distress syndrome (ARDS) and multiple organ failure. In a study of patients presenting at a hospital with sepsis, a correlation was found between TNF and IL-6 levels and septic complications (Terregino, et al., Ann. Emerg. Med., 35:26 (2000)).

Many conditions are thought to be associated directly or indirectly with inflammatory injury, and many commonly used therapeutic methods may also result in inflammatory injury either directly or indirectly. Exemplary types of inflammatory injury include traumatic injury, ischemia, and ischemia and reperfusion. Ischemic injury, or injury following ischemia, includes cellular damage resulting from an ischemic insult, which can occur upon the restriction or cessation of the flow of oxygen to an organ or tissue, such as by blockage or disconnection of one or more blood vessels. Ischemia can occur gradually or rapidly and can be either warm or cold.

Ischemia and reperfusion (I/R) injury is a pathophysiologic process whereby hypoxic organ damage is accentuated following return of blood flow and oxygen delivery following ischemia. The pathophysiology of ischemia and reperfusion injury includes both direct cellular damage as the result of the ischemic insult as well as delayed dysfunction and damage resulting from activation of inflammatory pathways.

An event of ischemia, including ischemia with reperfusion, can be controlled or uncontrolled. Controlled events can occur in vivo, ex vivo, or in vitro, during therapeutic treatment, such as a surgical procedure, during organ transplantation, during investigatory research, or in any circumstance under which they are deliberately induced. Most common controlled events include surgical procedures such as vascular surgery and cardiac bypass, as well as organ transplantation. Uncontrolled events can arise gradually, such as by accumulation of plaque in a coronary artery, or rapidly, such as during acute illness or upon injury. Ischemia and reperfusion can be controlled or uncontrolled independently. In some cases, uncontrolled ischemia can be treated with controlled reperfusion, such as in revascularization of a myocardial infarct, or in resuscitative treatment of hemorrhagic and/or hypovolemic shock. In other cases, transient episodes of ischemia followed by reperfusion are encountered during controlled procedures such as solid organ transplantation or elective liver resection, when inflow occlusion or total vascular exclusion can be used to minimize blood loss.

Inflammatory injury due to trauma, ischemia, and/or reperfusion are associated with, for example, anaphylaxis, apoptosis, burn injury, bursitis, cardiopulmonary bypass surgery, cerebral infarction, circulatory shock, compartment syndrome, congestive heart failure, conjunctivitis, coronary angioplasty blood vessel attachment, coronary artery obstruction, crushing injury, dermatitis, diseases involving angiogenesis, frostbite, graft rejection, gram negative bacteria-mediated circulatory shock, gram positive bacteria-mediated circulatory shock, hemodynamic shock, hemorrhage, hemorrhagic shock, hyperoxic alveolar injury, hypersensitivity, kidney failure, limb attachment or reattachment, liver failure, mycobacterial infection, myocardial infarction, myocardial ischemia, nephrotic syndrome, organ attachment or reattachment, organ reperfusion, periarteritis nodosa, radiation damage, septic shock, solid organ transplantation, spinal/head trauma and concomitant severe paralysis, stroke, swelling occurring after injury, and systemic inflammatory response syndrome (SIRS).

Methods of treating and preventing inflammation are known in the art, including administration of pharmaceuticals such as corticosteroids, non-steroidal anti-inflammatory drugs (NSAIDS), COX-2 inhibitors, or cytotoxic agents. An inhibitor of TNF production, HU-211, was shown to improve the outcome of closed brain injury in an experimental model (Shohami, et al, J Neuroimmunol. 72:169 (1997)). In an animal model, an IL-1 receptor antagonist was shown to inhibit fatty streak formation associated with atherosclerosis, a disease known to have an inflammatory component (Elhage et al., Circulation, 97:242 (1998)). U.S. Pat. No. 6,811,768 to Zapol, et al. describes the use of inhaled nitric oxide (NO) to decrease injury in pulmonary ischemia and reperfusion.

Preconditioning is another strategy for protection that has been studied extensively in many models of organ injury. By pre-exposing the organ to a minor stress at a pre-determined time point, preconditioning renders the organ less vulnerable to a subsequent injury. Previous efforts to precondition organs to ischemia and reperfusion have applied stimuli such as heat (Ishikawa, et al., J. Surg. Res. 97:178-184 (1999)), endotoxins including lipopolysaccharides (LPS) (Colletti, et al., J. Surg. Res. 57:337-343 (1994)), ischemia (Cavalieri, et al., Liver Transpl. 8:990-999 (2002)), and intermittent clamping (Murry, et al., Circulation, 74:1124-1136 (1986)). Preconditioning has also been undertaken using pharmacologic agents such as adenosine, IL-10, S-adenosyl-L-methionine, and cromakalim. See, e.g., Tsai, et al., Shock 21(3):195-209 (2004).

Despite the availability of certain regimens, treatments capable of diminishing inflammatory injury, as well as methods for preventing inflammatory injury and protecting an organ or tissue from injury, are needed.

BRIEF SUMMARY OF THE INVENTION

The invention provides a method of protecting an organ or tissue from injury comprising administering administration of a High Mobility Group Box 1 (HMGB1) protein to the organ or tissue, wherein the HMGB1 protein is administered in an amount effective to protect the organ or tissue from injury, and wherein the HMGB1 protein is administered within a time period sufficient to protect the organ or tissue from injury.

In one aspect, the invention provides a method of protecting an organ or tissue from ischemic injury comprising administering administration of an HMGB1 protein to the organ or tissue, wherein the HMGB1 protein is administered in an amount effective to protect the organ or tissue from injury, and wherein the HMGB1 protein is administered within a time period sufficient to protect the organ or tissue from injury.

In another aspect, the invention provides a method of protecting an organ or tissue from injury resulting from ischemia and reperfusion comprising administration of an HMGB1 protein to the organ or tissue prior to completion of reperfusion, wherein the HMGB1 protein is administered in an amount effective to protect the organ or tissue from injury.

In a further aspect, the invention also provides a method of protecting an organ or tissue from traumatic injury comprising administration of an HMGB1 protein to the organ or tissue, wherein the HMGB1 protein is administered in an amount effective to protect the organ or tissue from injury, and wherein the HMGB1 protein is administered within a time period sufficient to protect the organ or tissue from injury.

The invention also provides a method of preparing an organ or tissue for transplantation from a donor into a recipient comprising administration of an HMGB1 protein to the donor, wherein the organ or tissue is within the donor.

In a related aspect, the invention provides a method of preparing an organ or tissue for implantation into a recipient comprising administration of an HMGB1 protein to the organ or tissue ex vivo.

Additionally, the invention provides a composition for the prevention of injury to an organ following ischemia and reperfusion, comprising an HMGB1 protein and a pharmaceutically acceptable carrier.

The invention also provides a kit comprising a composition for the prevention of injury to an organ following ischemia and reperfusion and suitable instructions for administration, and optionally comprising a means for administration of the composition, wherein the composition comprises an HMGB1 protein and a pharmaceutically acceptable carrier.

Finally, the invention provides for use of an HMGB1 protein in preparation of a medicament for use in protecting an organ from injury caused by an event selected from the group consisting of ischemia, reperfusion, and trauma.

BRIEF DESCRIPTION OF THE SEVERAL VIEWS OF THE DRAWING(S)

Figure 1B:
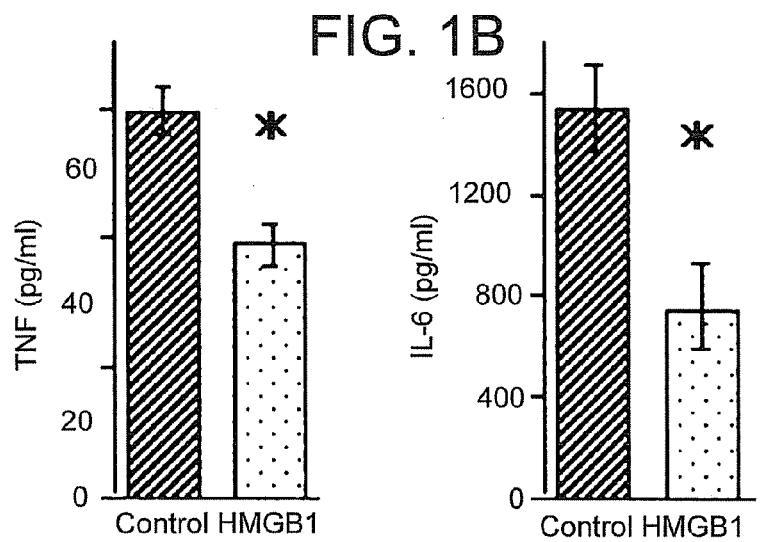
Figure 1C:
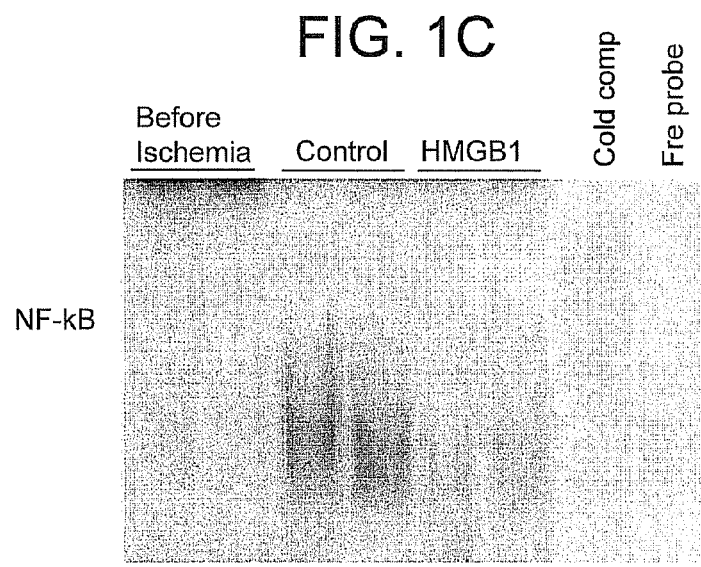

FIGS. 1A-C show effects of HMGB1 pretreatment on serum alanine aminotransferase (ALT) levels, serum TNF and IL-6 levels, and NF-κB activation. FIG. 1A depicts serum ALT levels for mice pretreated with rHMGB1 (2, 5, or 20 μg) or vehicle PBS i.v. one hour prior to ischemia, then subjected to ischemia and six hours of reperfusion. FIG. 1B depicts serum TNF and IL-6 levels for mice pretreated with 20 μg HMGB1 or vehicle, then subjected to ischemia and six hours of reperfusion. Data in FIGS. 1A and 1B reflect means±SE, n=six mice per group. *P<+0.05 versus mice subjected to I/R given vehicle PBS. FIG. 1C depicts NF-κB activation during hepatic I/R injury for mice pretreated with rHMGB1 or vehicle PBS before undergoing ischemia and one hour of reperfusion. Assay shown is representative of three experiments with similar results.

Figure 2A:
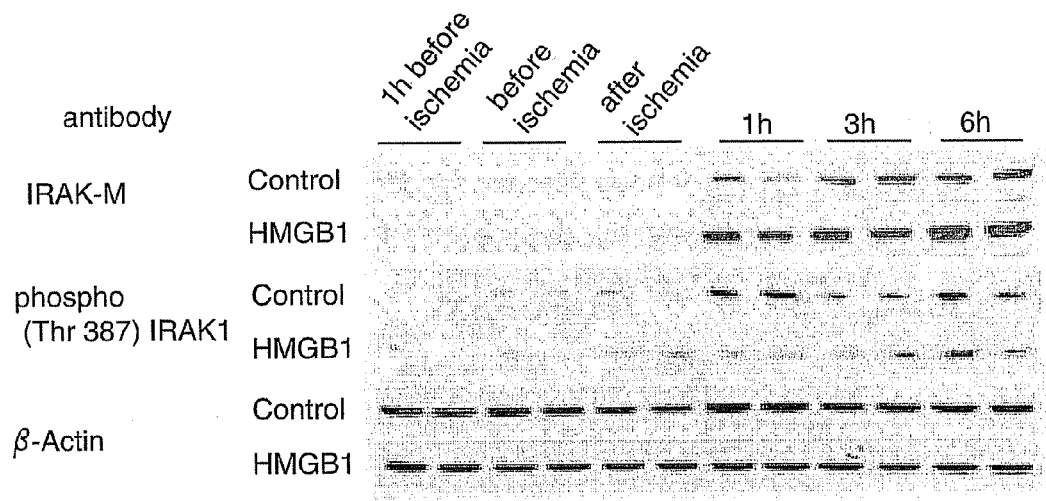
Figure 2B:
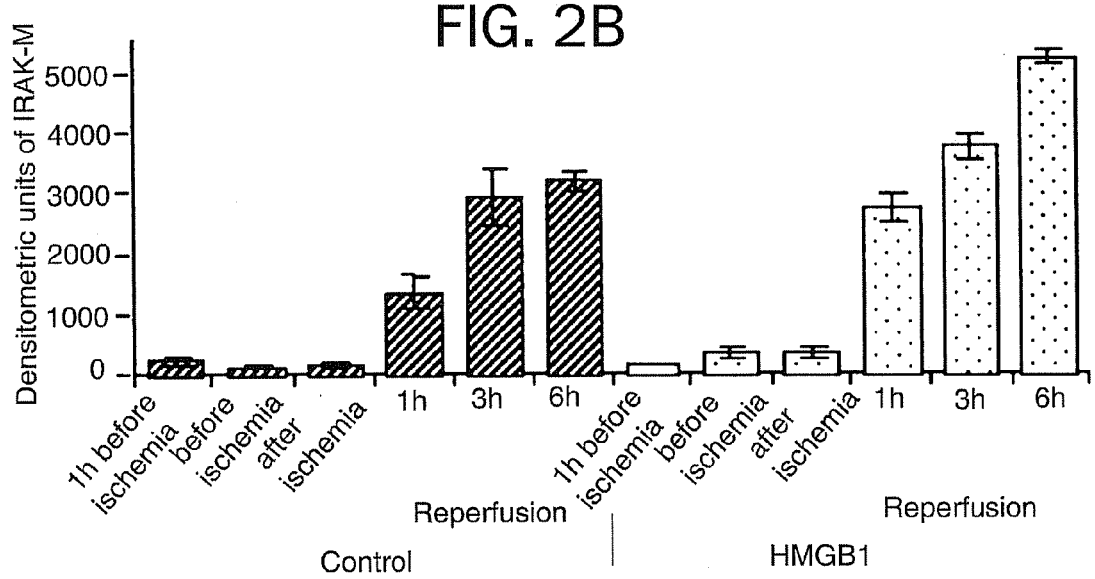

FIGS. 2A-B show effects of HMGB1 pretreatment on TLR signaling regulators. FIG. 2A depicts expression of IRAK-M and phosphorylated IRAK-1 in mice pretreated with 20 μg rHMGB1 or vehicle PBS at various time points, along with a β-actin control, Each lane provides results for a single animal. Blot shown is representative of three experiments with similar results. FIG. 2B shows levels of IRAK-M in mice treated with 20 μg rHMGB1 or vehicle PBS at several time points.

Figure 3A:
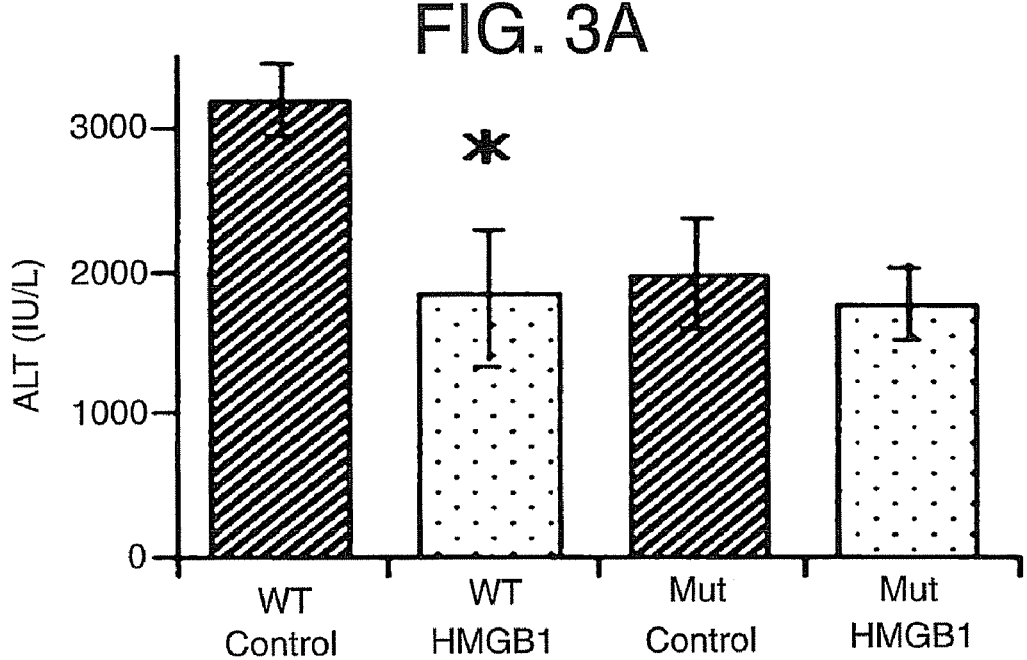
Figure 3B:
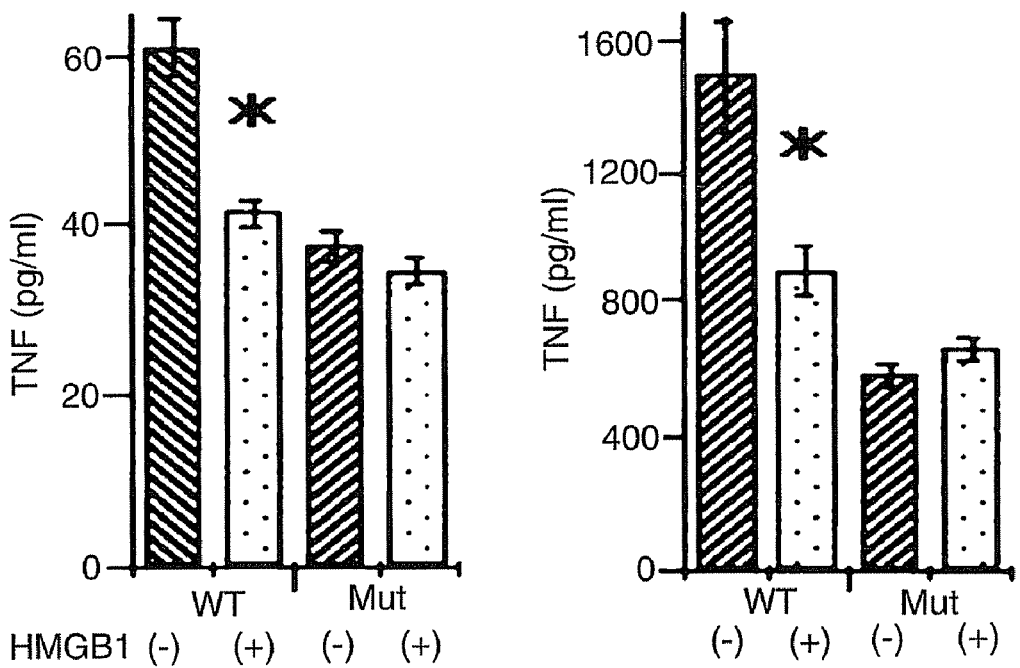

FIGS. 3A-B show effects of HMGB1 pretreatment on wild type mice as compared to TLR4-mutant mice. FIG. 3(A) depicts serum ALT levels for TLR4-mutant mice (C3H/HeJ) and their wild-type mice counterpart (C3H/HeOuj), pretreated with 20 μg rHMGB1 or vehicle PBS one hour prior to ischemia. FIG. 3B depicts serum TNF and IL-6 levels for TLR4-mutant mice and their wild-type counterparts, pretreated with 20 μg HMGB1 or vehicle PBS, then subjected to ischemia and six hours of reperfusion. Data in FIGS. 3A and 3B reflect means±SE, n=seven mice per group. *P<0.05 versus TLR4 wild-type mice subjected to I/R given vehicle.

Figure 4:
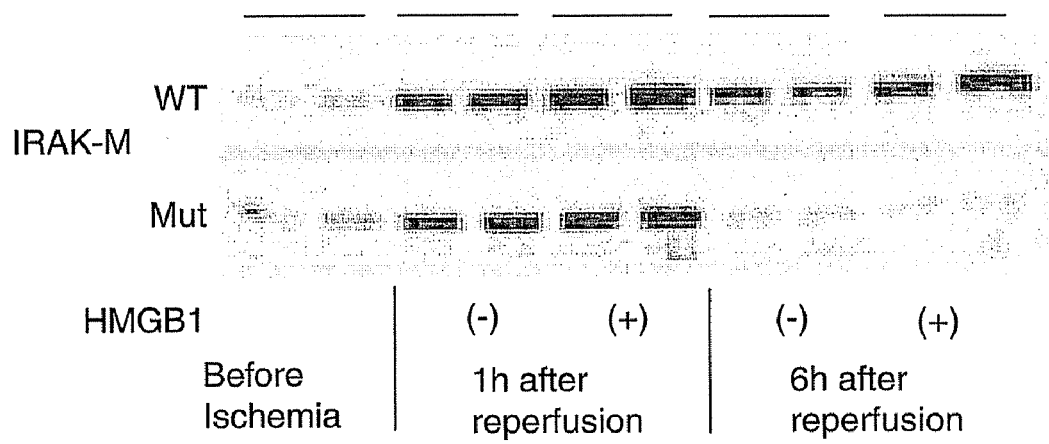
Figure 4:
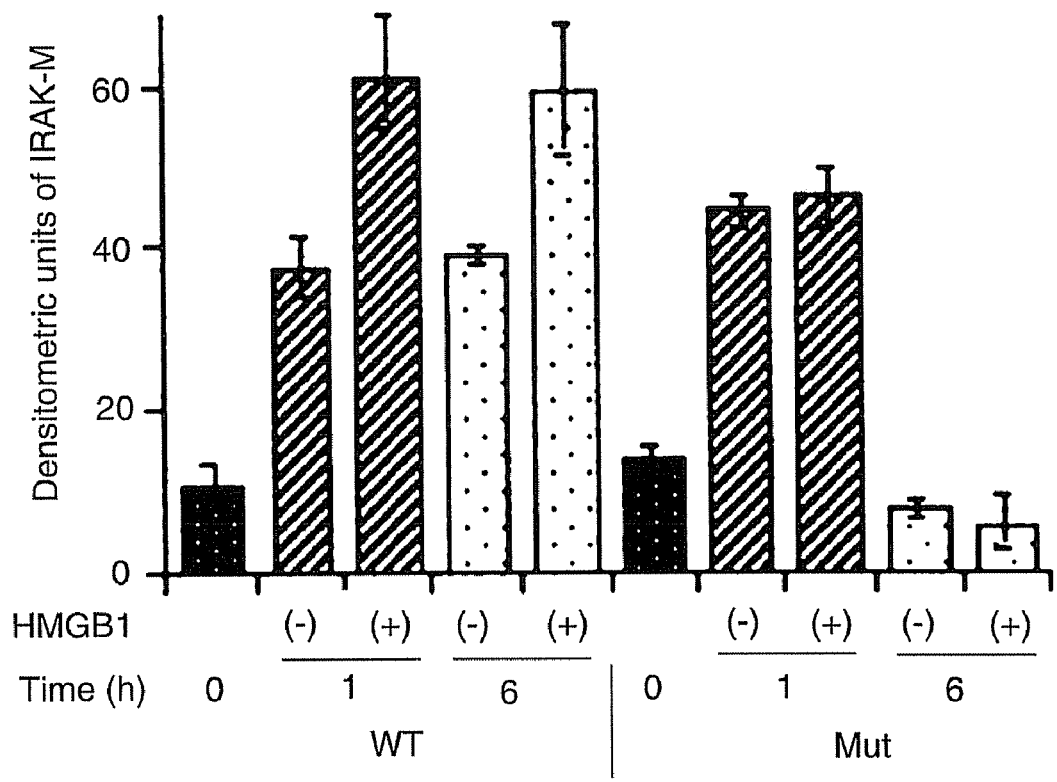

FIG. 4 depicts IRAK-M levels at 1 and 6 hours after reperfusion in TLR4-mutant mice as compared to wild type mice, with all mice pretreated with 20 μg rHMGB1 or vehicle PBS one hour prior to ischemia. Each lane provides results for a separate animal. Blot shown (top panel) is representative of three experiments with similar results. The lower panel graphically displays densitometric units of IRAK-M.

FIG. 5 depicts serum ALT levels for mice pretreated with LPS (5 ng or 5 μg) or vehicle PBS i.v. one hour prior to ischemia, then subjected to ischemia and six hours of reperfusion. Serum ALT levels were analyzed as a measure of hepatocellular injury. Data reflect means±SE, n=six mice per group. *P<0.05 versus mice subjected to I/R given vehicle PBS. per group. *P<0.05 versus mice subjected to I/R given vehicle PBS.

DETAILED DESCRIPTION OF THE INVENTION

HMGB1 Proteins

The present invention relates to methods and compositions involving HMGB1 proteins. In the context of the present invention, an "HMGB1 protein" is any polypeptide having the sequence of a vertebrate HMGB1 protein, or a polypeptide having a related sequence (such as HMGB2), as well as variant, analog, homolog, and fragments thereof that have sufficient activity to be suitably employed to protect injury as discussed herein.

In one embodiment, the HMGB1 protein is a polypeptide having the sequence of a mammalian HMGB1 protein such as GenBank Accession Number AAA40729 (SEQ ID NO:2). The HMGB1 protein can have the sequence of human HMGB1, such as GenBank Accession Number AAV38961 or CAG33144. Alternatively, the HMGB1 protein can have a sequence as disclosed in GenBank Accession Numbers AAB08987 (human), AAH88402 (rat), P07155 (rat), AAA20508 (mouse), AAP36330 (human synthetic), AAC27651 (*spalax ehrenbergi*), XP516325 (chimpanzee), AAI02930 (*bos taurus*), AAA31050 (*sus scrofa*), XP484795 (mouse), CAA76978 (*gallus gallus*), AAH63332 (*xenopus tropicalis*), AAA64970, S29857, P09429, or NP_002119, the entire teachings of which are incorporated herein by reference. It should be noted that HMGB1 is highly conserved among species.

Examples of proteins related to HMGB1 that can be employed as the HMBG1 protein in the context of the present invention include, but are not limited to mammalian HMGB2, HMG-2A, HMG14, HMG17, HMG I and HMGY; nonmammalian HMG T1 and HMG T2 (rainbow trout), HMG-X (*Xenopus*), HMG D/Z (*Drosophila*), yeast polypeptides NHP10 protein (HMG protein homolog NHP 1) and nonhistone chromosomal protein; HMG 1/2 like protein (wheat, maize, soybean); upstream binding factor (UBF-1)) single-strand recognition protein (SSP) or structure-specific recognition protein; the HMG homolog TDP-1; mammalian sex-determining region Y protein (SRY, testis-determining factor); fungal proteins: mat-1, ste 11 and Mc 1; SOX 14 (as well as SOX 1-3, 6, 8, 10, 12 and 21); lymphoid specific factor (LEF-1); T-cell specific transcription factor (TCF-1); and SP100-HMG nuclear autoantigen.

An HMGB1 protein can also be or comprise a biologically-active variant, analog, homolog, or derivative of full length, wild-type (i.e., native) HMGB1 and proteins related to HMGB1 (including the examples disclosed herein) or fragment thereof. By "biologically active" it is meant that a variant, analog, homolog, or derivative of native HMGB1 and proteins related to HMGB1 or fragment thereof possesses sufficient activity to be suitably employed to protect injury as discussed herein.

HMGB1 variants are polypeptides that retain at least one biological activity of native HMGB1 or proteins related to HMGB1 but differ in amino acid sequence. A variant can be substantially identical to a native protein as described above. A sequence can also be a variant if the DNA encoding the sequence is capable of hybridizing under stringent conditions to the complement of DNA encoding a native HMGB1 protein. Stringent conditions are conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions can be selected to be about 5-10° C. lower than the thermal melting point ($T_m$) for the specific sequence at a defined ionic strength pH. The $T_m$ can be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions can be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions can also be achieved with the addition of destabilizing agents such as formamide. For selective or specific hybridization, a positive signal can be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

HMGB1 homologs are polypeptides native to different species that retain biological activity (e.g., human and porcine insulin, human and salmon calcitonin, etc.) or intraspecies isomers of a polypeptide (protein "families" such as the cytochrome P450 family). Non-limiting examples of some HMGB1 homologs are listed above.

HMGB1 analogs are polypeptides that differ in amino acid sequence from native HMGB1 but retain at least one biological activity of a native HMGB1 protein, as described above. These analogs can differ in amino acid sequence from HMGB1, e.g., by the insertion, or substitution of amino acids. Preferably, a substitution is conservative, A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge, and include the following values: alanine (+1.8), arginine (−4.5), asparagine (−3.5), aspartate (−3.5), cysteine/cystine (+2.5), glycine (−0.4), glutamate (−3.5), glutamine (−3.5), histidine (−3.2), isoleucine (+4.5), leucine (+3.8), lysine (−3.9), methionine (+1.9), phenylalanine (+2.8), proline (−1.6), serine (−0.8), threonine (−0.7), tryptophan (−0.9), tyrosine (−1.3), and valine (+4.2). It is known in the art that amino acids of similar hydropathic indexes can be substituted and still retain protein function. Preferably, amino acids having hydropathic indexes of +/−2 are substituted.

The hydrophilicity of amino acids can also be used to reveal substitutions that would result in proteins retaining biological function. A consideration of the hydrophilicity of amino acids in the context of a polypeptide permits calculation of the greatest local average hydrophilicity of that polypeptide, a useful measure that has been reported to correlate well with antigenicity and immunogenicity. U.S. Pat. No. 4,554,101, incorporated herein by reference. Hydrophilicity values for each of the common amino acids, as reported in U.S. Pat. No. 4,554,101, are: alanine (−0.5), arginine (+3.0), asparagine (+0.2), aspartate (+3.0.+−0.1), cysteine (−1.0), glycine (0), glutamate (+3.0.+−0.1), glutamine (+0.2), histidine (−0.5), isoleucine (−1.8), leucine (−1.8), lysine (+3.0), methionine (−1.3), phenylalanine (−2.5), proline (−0.5.+−0.1), serine (+0.3), threonine (−0.4), tryptophan (−3.4), tyrosine (−2.3), and valine (−1.5). Substitution of amino acids having similar hydrophilicity values can result in proteins retaining biological activity, for example immunogenicity, as is understood in the art. Preferably, substitutions are performed with amino acids having hydrophilicity values within +/−2 of each other. Both the hyrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

Additionally, computerized algorithms are available to assist in predicting amino acid sequence domains likely to be accessible to an aqueous solvent. These domains are known in the art to frequently be disposed towards the exterior of a protein, thereby potentially contributing to binding determinants, including antigenic determinants. Having the DNA sequence in hand, the preparation of such analogs is accomplished by methods well known in the art (e.g., site-directed) mutagenesis and other techniques.

HMGB1 derivatives are proteins or peptides that differ from native HMGB1 in ways other than primary structure (i.e., amino acid sequence). By way of illustration, ECM signaling molecule derivatives can differ from native HMGB1 by being glycosylated, one form of post-translational modification. For example, polypeptides can exhibit glycosylation patterns due to expression in heterologous systems. The various polypeptides of the present invention, as described above, can be provided as discrete polypeptides or be linked, e.g., by covalent bonds, to other compounds. Thus, other HMGB1 derivatives include, but are not limited to, fusion proteins having a covalently modified N or C-terminus, PEGylated polypeptides, polypeptides associated with lipid moieties, alkylated polypeptides, polypeptides linked via an amino acid side-chain functional group to other polypeptides or chemicals, and additional modifications as would be understood in the art. If these polypeptides retain at least one biological activity of a native HMGB1 protein, then these polypeptides are HMGB1 derivatives in the context of the invention, and if they also have sufficient activity to be suitably employed to protect injury as discussed herein, then such HMGB1 derivatives also are HMGB1 proteins.

Preferably, a variant, analog, homolog, or derivative of a native HMGB1 or protein related to HMGB1 has at least 60%, or more preferably, 70%, 75%, 80%, 85%, 90%, 95%, 99%, or 100% similarity to the native sequence. More preferably, a variant, analog, homolog, or derivative of a native HMGB1 or protein related to HMGB1 has at least 60%, or more preferably, 70%, 75%, 80%, 85%, 90%, 95%, 99%, or 100% sequence identity to the native sequence. A sequence is substantially identical if it is at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more amino acids.

Sequence identity and/or similarity can be determined using standard BLAST parameters or any other measure of sequence identity and/or similarity as known to one of ordinary skill in the art. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation.

Fragments of HMGB1, a protein related to HMGB1, or of a variant, analog, or homolog thereof that retain one or more activities of native HMGB1, and which have sufficient activity to protect injury as discussed herein, also are suitable HMGB1 proteins for use in the context of the present invention. Biologically active fragments of HMGB1 can be naturally occurring or non-naturally occurring, including recombinant fragments of a HMGB1 or a protein related to HMGB1. Due to the high level of conservation of HMGB1 proteins, it will be expected that one skilled in the art will identify biologically active sequences from the various proteins disclosed above based on the identification of the regions corresponding to the A box and B box. Preferably, a fragment for use in the present invention comprises a sequence of at least 5, such as at least 10, and more preferably at least 15 or at least 20, such as at least 30 or a least 50 contiguous amino acids of a native HMGB1, a protein related to HMGB1, or of a variant, analog, or homolog thereof. A fragment can include a sequence of substantially all of the native HMGB1, a protein related to HMGB1, or of a variant, analog, or homolog thereof or it can comprise less than substantially all of native HMGB1, a protein related to HMGB1, or of a variant, analog, or homolog thereof. Thus, for example, a fragment can comprise a sequence of up to about 150, such as up to about 125 or up to about 100, or up to about 75 contiguous amino acids of a native HMGB1, a protein related to HMGB1, or of a variant, analog, or homolog thereof.

Exemplary fragments include polypeptides corresponding to the portion of HMGB1 designated the "A box" as well as the portion of HMGB1 designated the "B box." Sequences of A box fragments can correspond approximately to amino acids 4-89 of a full length HMGB1 protein, and sequences of B box fragments can correspond approximately to amino acids 90-174, as described in Bianchi, et al., EMBO J. 11(3): 1055-1063 (1992). Fragments can comprise all or a portion of the A box, all or a portion of the B box or comprise portions of both the A box and the B box. Fragments can comprise one or more of the sequences disclosed at SEQ ID NO:25-26. Preferably, fragments comprise the B box or a portion of the B box such as SEQ ID NO:26. Fragments can also comprise amino acids 1-20 of the B box region of any HMGB1 protein.

HMGB1 is a nuclear protein involved in transcriptional activation and DNA folding. In addition to its nuclear role, extracellular HMGB1 has been shown to be a critical mediator of the innate immune response to infection and injury, itself having cytokine properties. HMGB1 has been shown to be a late mediator in the inflammatory response, induced by early proinflammatory cytokines such as tumor necrosis factor (TNF) and IL-1. Wang, et al., Science, 285:248-251 (1999). Additionally, HMGB1 can also play a role as an early mediator following acute, local organ injury. Tsung, et al., J. Exp. Med. 201(7): 1135-1143 (2005).

Despite its cellular ubiquity, the presence of serum (extracellular) HMGB1 indicates injury. Serum levels of HMGB1 are undetectable in normal human patients. Tracey, et al., WO 00/47104. Elevated levels of HMGB1 can occur in conjunction with sepsis, a condition associated with activation of pro-inflammatory cytokines, as well as hemorrhagic shock. Andersson, et al., J. Exp. Med. 192(4):565-570 (2000). Elevated HMGB1 levels have also been associated with injury following ischemia and reperfusion (I/R). Tsung, et al., J. Exp. Med. 201(7):1135-1145 (2005). The most dramatically elevated HMGB1 levels can be associated with lethality.

Previous attempts to decrease or inhibit HMGB1 have included administration of antibodies of HMGB1 as well as administration of certain fragments of HMGB1. For example, U.S. Pat. Pub. 2003/0060410 by Tracey, et al. describes the use of certain HMGB1 fragments, specifically A box fragments, as inhibitory polypeptides and the use of antibodies to decrease HMGB1 levels in a sepsis model. In the context of HMGB1-mediated atherosclerosis and restenosis, HMGB1 antibodies, inhibitory HMGB1 fragments and analogs, as well as four-way DNA have been suggested as possible antagonists and/or inhibitors for HGMB1. U.S. Pat. Pub. 2004/0136979 by Bianchi, et al.

Exogenous administration of HMGB1 has previously been found to be detrimental, and often lethal. Wang, et al., Science, 285:248-251 (1999). Intratracheal administration of HMGB1 has been shown to cause acute lung injury and lethality. Abraham, et al., J. Immunol. 165:2950-2954 (2000). Administration of HMGB1 to mice following reperfusion worsened I/R injury as compared to sham-treated and untreated control animals. Tsung, et al., J. Exp. Med. 201(7): 1135-1145 (2005). Administration of certain fragments of HMGB1, specifically B box fragments, has been shown to recapitulate the toxicity and lethality of full length HMGB1 in vivo. Li, et al., Mol. Med. January/February 2003: 37-45.

Accordingly, the present inventive method involving the administration of an HMGB1 protein to protect against inflammation and organ injury following events such as ischemia, reperfusion, and/or trauma is quite surprising.

The Inventive Method

The invention provides a method of protecting an organ or tissue from injury caused by ischemic insults, reperfusion following ischemia, and trauma. These events can be either controlled or uncontrolled, as noted above.

The HMGB1 protein can be administered to any organ or tissue in need thereof at the discretion of one skilled in the art. Preferably, the organ or tissue is selected from the group consisting of a brain, a heart, a liver, a portion of a liver, a lung, a portion of a lung, a kidney, an intestine, a portion of an intestine, a pancreas, an eye, a muscle, a portion of a muscle, a bone, a portion of a bone, a nerve tissue, a vascular tissue, or an epithelial tissue. More preferably, the organ or tissue is a heart, a brain, a liver or a portion of a liver, or a bone or a portion of a bone.

Depending on the desired application of the inventive method, the organ or tissue can be in a host (in vivo), or in vitro. The method can have veterinary or research applications, but preferably it is employed in the medical context, in which instance the host (and the organ or tissue) preferably is human. However, in veterinary or research applications, and also in the context of xenotransplantation into a human recipient, the host can be a non-human animal (such as a mouse, rat, rabbit, cow, pig, chimpanzee, cat, or dog).

In one embodiment of the present invention, a method is provided for protecting an organ or tissue from ischemic injury comprising administration of an HMGB1 protein to the organ or tissue, wherein the HMGB1 protein is administered in an amount effective to protect the organ or tissue from injury, and wherein the HMGB1 protein is administered within a time period sufficient to protect the organ or tissue from injury. Conditions associated with uncontrolled ischemia include stroke and certain cardiac disorders, such as myocardial infarct. Uncontrolled ischemia can also occur during acute occlusion of blood supply to organs or limbs. Thus, for mitigating the effects of stroke, for example, the inventive method can comprise administering the HMGB1 protein to the affected area (e.g., brain or region of the brain) within a brief time following the stroke. Similarly, for treatment of cardiac ischemia, the inventive method comprises administering the HMBG1 to the affected area of the heart shortly after ischemia.

In another embodiment of the present invention, a method is provided for protecting an organ or tissue from injury resulting from ischemia and reperfusion comprising administration of an HMGB1 protein to the organ or tissue prior to completion of reperfusion, wherein the HMGB1 protein is administered in an amount effective to protect the organ or tissue from injury. The methods of the present invention can preferably be employed in any medically appropriate circumstance that results in or that can result in injury due to ischemia and/or reperfusion, such as can occur when the ischemia and reperfusion occur during a surgical procedure or during organ transplantation. Examples of conditions or procedures generating a risk of injury attributable to reperfusion following ischemia include liver resection; revascularization following myocardial infarction, such as by thrombolytic therapy, stenting, or surgical repair; revascularization following stroke, such as by thrombolytic therapy or surgical repair; or revascularization following vascular injury including repair or reattachment of a limb following ischemic injury or surgical repair of an aneurysm.

Organ transplantation is a preferred application of the inventive method. In this context, the method involves harvesting an organ from a donor (involving ischemia) and transplanting the organ into a recipient (involving reperfusion). The donor can be a living donor (e.g., of a kidney, skin graft, or other organ) or a cadaver donor, If the donor is a cadaver donor, the donor can be a heart-beating or a non-heart-beating cadaver donor. The donor (and the organ) can be of any desired species, typically mammalian, but most preferably is allospecific to the recipient. However, the method can be employed in the xenotransplantation context, in which case the donor (and organ) are of a different species than the recipient.

When employed to prevent injury resulting from ischemia and reperfusion during transplantation of an organ from a donor or recipient, the HMGB1 protein can be administered to the organ prior to harvest or post harvest. For example, the HMGB1 protein can be administered to the recipient prior to or after the organ has been implanted (e.g., prior to reperfusion or during reperfusion of the organ), such that the HMGB1 protein permeates a portion of the vasculature of the organ.

Alternatively, the HMGB1 protein can be administered to the donor (e.g., systemically or locally to the organ in question) prior to ischemia such that it permeates a portion of the vasculature of the organ to be harvested. In this sense, the inventive method can be used to prepare the organ or tissue for transplantation from the donor into the recipient.

The method also can be employed to prepare an organ or tissue for implantation into a recipient by administering the HMGB1 protein to the organ or tissue ex vivo (i.e., after it has been harvested from the donor but before implantation into the recipient). For example, the organ can be perfused with a composition comprising the HMGB1 protein for a period of time ex vivo.

In another embodiment of the present invention, a method is provided for protecting an organ or tissue from traumatic injury. In accordance with this aspect of the invention, the method comprises administration of an HMGB1 protein to the organ or tissue, wherein the HMGB1 protein in an amount effective to protect the organ or tissue from injury, and wherein the HMGB1 protein is administered within a time period sufficient to protect the organ or tissue from injury. Traumatic injury that can be treated in accordance with the inventive method can include, for example, bone fractures, burns, lacerations, blunt trauma, blast injuries, traumatic amputations, crushing injuries, traumatic hematoma or aneurysm, as well as other injuries known to one skilled in the art. Additionally, traumatic injury includes damage to organs or tissue that can occur during surgical procedures, regardless of whether ischemia and/or reperfusion occurs.

Dosage and Administration

In the performance of the inventive method, the HMGB1 protein can be administered before, during, or after the trauma or ischemia, provided that it is administered in sufficient time to achieve its protective effect. Preferably, the HMGB1 protein is administered prior to about one hour after trauma or ischemia. The HMGB1 protein can be administered prior to about 45, 30, 15, 10, or 5 minutes after injury. If the event leading to injury includes reperfusion, the HMGB1 protein is most preferably administered before reperfusion is completed. If an event leading to trauma or ischemia is controlled, the HMGB1 protein is preferably administered prior to the trauma or ischemia. The HMGB1 protein can be administered about 5, 10, 15, 30, or 45 minutes prior to trauma or ischemia. Preferably, the HMGB1 protein is administered about one hour prior to the trauma or ischemia. In some cases, it can be advantageous to administer the HMGB1 protein more than about one hour prior to the trauma or ischemia.

In the performance of the inventive method, the HMGB1 protein can be administered in a dosage of about 5 µg to about 35 mg, or greater than about 35 mg. The dosage can be about 5 µg to about 20 µg, about 20 µg to about 1 mg, or about 1 mg to about 10 mg. In some embodiments, the dosage is preferably about 10 mg to about 35 mg. In other embodiments, the dosage can be greater than 35 mg. One skilled in the art can readily select a correct dosage based on the circumstances of treatment.

If the organ or tissue is located in the host (which, in the context of transplantation, can be a donor or a recipient), the HMGB1 protein can be administered systemically to the host. The HMGB1 protein can be administered by a route selected from the group consisting of intravenous, intramuscular, intraperitoneal, percutaneous, subcutaneous, topical, transmucosal, oral, or by another route known to one skilled in the art. Preferably, the HMGB1 protein is formulated for administration by injection. It is particularly preferred to formulate the HMGB1 protein for rapid delivery by methods known to one skilled in the art. As an alternative to systemic administration, or in addition to systemic administration, the HMGB1 protein can be administered locally to the organ or tissue. The HMGB1 protein can be administered by injection, catheter infusion, surface application, immersion in a bath, or by other means known to one skilled in the art. For example, HMGB1 can be administered directly to a heart during treatment for myocardial infract by injection to a blood vessel in combination with angioplasty, or by application of a medicated stent.

Composition

For use in the inventive method, the invention further provides a composition comprising an HMGB1 protein for the prevention of injury to an organ or tissue due to ischemia, reperfusion, or trauma. In this sense, the invention pertains to the use of an HMGB1 protein in preparation of a medicament for use in protecting an organ or tissue from injury caused by an event selected from the group consisting of ischemia, reperfusion, and trauma. The composition comprises an HMGB1 protein and a pharmaceutically acceptable carrier. The composition can be formulated for administration by a route selected from the group consisting of intravenous, intramuscular, intraperitoneal, percutaneous, subcutaneous, topical, or oral. The composition also can comprise additional components such as diluents, adjuvants, excipients, preservatives, and pH adjusting agents, and the like.

Formulations suitable for local or systemic injectable administration include aqueous and nonaaqueous, isotonic sterile injection solutions, which can contain anti-oxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, or tablets.

Sterile injectable solutions can be prepared by incorporating the active compound in the required amount in an appropriate solvent with one or a combination of ingredients enumerated above, as required, followed by filtered sterilization. Preferably solutions for injection are free of endotoxin. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

The active ingredients can also be entrapped in microcapsules prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980). Specifically, liposomes containing the HMGB1 protein can be prepared by such methods as described in Epstein et al., Proc. Natl. Acad. Sci. USA, 82; 3688 (1985); Hwang et al., Proc. Natl. Acad. Sci. USA, 77:4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Polypeptides of the present invention can be conjugated to the liposomes as described in Martin et al., J. Biol. Chem., 257:286-288 (1982) via a disulfide interchange reaction.

Administration into the airways can provide either systemic or local administration, for example to the trachea and/or the lungs. Such administration can be made via inhalation or via physical application, using aerosols, solutions, and devices such as a bronchoscope. For inhalation, the compositions herein are conveniently delivered from an insufflator, a nebulizer, a pump, a pressurized pack, or other convenient means of delivering an aerosol, non-aerosol spray of a powder, or noon-aerosol spray of a liquid. Pressurized packs can comprise a suitable propellant such a liquefied gas or a compressed gas. Liquefied gases include, for example, fluorinated chlorinated hydrocarbons, hydrochlorofluorocarbons, hydrochlorocarbons, hydrocarbons, and hydrocarbon ethers. Compressed gases include, for example, nitrogen, nitrous oxide, and carbon dioxide. In particular, the use of dichlorodifluoromethanie, trichlorofluoromethane, dichlorotetrafluoroethane, carbon dioxide or other suitable gas is contemplated. In the case of a pressurized aerosol, the dosage unit can be determined by providing a valve to deliver a controlled amount. In administering a dry powder composition, the powder mix can include a suitable powder base such as lactose or starch. The powder composition can be presented in unit dosage form such as, for example, capsules, cartridges, or blister packs from which the powder can be administered with the aid of an inhalator or insufflator.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays, inhaled aerosols, suppositories, mouthwashes, rapidly dissolving tablets, or lozenges.

For transdermal administration, the active compounds are formulated into ointments, salves, gels, foams, or creams as generally known in the art.

The pharmaceutical compositions can be delivered using drug delivery systems. Such delivery systems include hyaluronic acid solutions or suspensions of collagen fragments. The drugs can be formulated in microcapsules, designed with appropriate polymeric materials for controlled release, such as polylactic acid, ethylhydroxycellulose, polycaprolactone, polycaprolactone diol, polylysine, polyglycolic, polymaleic acid, poly[N-(2-hydroxypropyl)methylacrylamide] and the like. Particular formulations using drug delivery systems can be in the form of liquid suspensions, ointments, complexes to a bandage, collagen shield or the like.

In another embodiment, the invention provides a kit comprising a the inventive composition and suitable instructions for administration. The kit can and optionally comprise a means for administration of the composition, such as, for example, a needle, catheter, cannula, pump, transdermal patch, nebulizer, or other delivery means suitable to the mode of administration. The kit facilitates ready administration of the composition or practice of the inventive method and can be deployed for use in emergency settings.

While one of skill in the art is fully able to practice the instant invention upon reading the foregoing detailed description, the following examples will help elucidate some of its features. In particular, they demonstrate the effects of HMGB1 pretreatment on several indicators of I/R injury including levels of serine alanine aminotransferase, cytokines IL-6 and TNF, NF-κB, and IRAK-M. They demonstrate the effect of HMGB1 pretreatment on TLR4 signaling in TLR4-mutant and wild type mice. Additionally, they demonstrate that LPS does not protect against I/R injury to liver tissue. Of course, as these examples are presented for purely illustrative purposes, they should not be used to construe the scope of the invention in a limited manner, but rather should be seen as expanding upon the foregoing description of the invention as a whole.

The procedures employed in these examples, such as surgery, histopathology, and molecular analysis of proteins and polynucleotides, are familiar to those of ordinary skill in this art. As such, and in the interest of brevity, experimental details are not recited in detail.

Example 1

This example demonstrates that HMGB1 treatment can protect against hepatocellular injury caused by I/R.

Male wild-type (C57BL/6; C3H/HeOuj) and TLR4-defective (C3H/HeJ) mice (8-12 weeks old) were purchased from the Jackson Laboratory (Bar Harbor, Me.). All animals were maintained in a laminar-flow, specific pathogen-free atmosphere at the University of Pittsburgh. Animal protocols were approved by the Animal Care and Use committee of the University of Pittsburgh and the experiments were performed in adherence to the National Institutes of Health Guidelines for the use of Laboratory Animals.

Mice received either recombinant HMGB1 or vehicle PBS intravenously at various concentrations one hour prior to ischemia. Recombinant HMGB1 was prepared as described in Yang, et al., *Proc Natl Acad Sci USA* 101:296-301 (2004). The HMGB1 used for these studies contained undetectable amounts of LPS as measured by the chromogenic *Limulus amoebocyte* lysate assay (Associates of Cape Cod or Bio-Whittaker).

A non-lethal model of segmental (70%) hepatic warm ischemia was used as described in Tsung, et al., *J Exp Med* 201:1135-43 (2005). After induction of anesthesia, all structures in the portal triad (hepatic artery, portal vein, and bile duct) to the left and median liver lobes were occluded with a microvascular clamp (Fine Science Tools, San Francisco, Calif.) for 60 minutes, and reperfusion was initiated by removal of the clamp. Temperature was monitored by rectal temperature probe and was maintained at 37° C. by means of a warming pad and heat lamp. Animals were sacrificed at predetermined time points after reperfusion for serum and liver samples.

Sixty minutes of warm hepatic ischemia followed by 6 hours of reperfusion resulted in increased serum ALT levels, decreased cytokine levels, decreased activation of NF-κB, and increased expression of IRAK-M as compared to control mice subjected to I/R.

Levels of serum ALT, an indicator of hepatocelluar injury, were measured using the Opera Clinical Chemistry System (Bayer Co., Tarrytown, N.Y.) to assess hepatic function and cellular injury following liver ischemia. Pretreatment with 5 to 20 μg of rHMGB1 resulted in significant protection from hepatic injury in a dose dependent manner (FIG. 1A). Liver histology confirmed the sALT estimation of liver damage (data not shown). Severe sinusoidal congestion and hepatocellular necrosis was present in liver tissue from control mice whereas minimal damage was noted in samples from HMGB1 treated mice.

To determine levels of inflammatory cytokines, serum levels of cytokines TNF and IL-6 were measured after I/R using ELISA kits from Biosource International (Camarillo, Calif.). Compared to sham-treated animals, liver I/R in control animals resulted in increased levels of TNF and IL-6 six hours after reperfusion (data not shown). However, animals pretreated with HMGB1 exhibited lower levels of serum TNF and IL-6 compared to control animals subjected to I/R (FIG. 1B).

To measure activation of NFκB, a transcription factor involved in signal transduction of a variety of extracellular stress stimuli such as proinflammatory and protective responses in the liver, nuclear extracts were prepared from the ischemic livers and subjected to electrophoretic mobility shift assay (EMSA) as described in Tsung, et al., *J. Exp. Med.* 201:1135-43 (2005). NF-κB DNA binding increased in the ischemic liver one hour after reperfusion in control mice when compared to sham-treated animals (FIG. 1C). Mice pretreated with HMGB1 exhibited less NF-κB DNA binding activity. The specificity of the NF-κB bands were confirmed by cold competition in the presence of excess unlabeled NF-κB consensus motif.

IRAK-M protein expression was upregulated in the livers in both control mice and in pretreated mice. Western blot analysis for IRAK-M and phosphorylated IRAK-1 was performed for hepatic protein lysates of the ischemic lobes at the time points shown (FIG. 2A). Mice pretreated with HMGB1 exhibited higher hepatic IRAK-M levels after reperfusion than control mice (FIGS. 2A-B). In contrast, control mice exhibited increased levels of phosphorylated IRAK-1 after reperfusion. In mice pretreated with HMGB1, phosphorylated IRAK-1 levels were lower than in control mice. Based on these results, lower IRAK-1 phosphorylation in the livers of mice pretreated with HMGB1 was associated with increased hepatic IRAK-M expression in the pretreated mice after I/R.

Example 2

This example demonstrates that pretreatment with HMGB1 can protect against I/R injury relating to TLR4 signaling.

TLR4-mutant (C3H/HeJ) mice and wild-type control (C3H/HeOuj) mice were subjected to liver I/R with or without HMGB1 pretreatment as described in Example 1. Serum ALT levels, serum TNF and IL-6 levels, and hepatic IRAK-M expression were measured.

Based on serum ALT levels, control TLR4-mutant mice were protected from hepatic I/R injury compared to control wild-type mice. (FIG. 3A). The protective effect of HMGB1 pretreatment as seen in wild-type mice was not increased in TLR-4 mutant mice; TLR4-mutant mice were protected at the same level regardless of whether they received HMGB1 pretreatment. Although the liver damage in TLR-4 mutant mice is approximately 50% less than in control wild-type mice, it is still much greater than sham animals.

TLR4 wild-type mice treated with HMGB1 exhibited decreased circulating TNF and IL-6 levels compared to control I/R animals, but TLR4-mutant mice treated with HMGB1 showed no difference in levels of these cytokines when compared to mutant mice not receiving HMGB1 (FIG. 3B).

When hepatic IRAK-M was measured under conditions as described in Example 1, wild-type mice pretreated with HMGB1 had higher expression of hepatic IRAK-M compared to wild-type control mice (FIG. 4). However, there was no significant difference in IRAK-M expression between TLR4-mutant animals treated with or without HMGB1.

Example 3

This example demonstrates that pretreatment with lipopolysaccharides (LPS) does not protect against I/R injury to liver tissue.

Preconditioning during I/R can be triggered by diverse stimuli, including endotoxemia. To exclude a role for LPS in the protective effects seen with HMGB1 pretreatment, mice were treated with varying doses of LPS and subjected to liver I/R. LPS from $E.\ coli$ 0111:B4 was obtained from Sigma (St. Louis, Mo.). Unlike mice pretreated with HMGB1, the mice pretreated with either 5 ng or 5 μg of LPS did not exhibit a reduction in I/R-induced damage compared to control animals (FIG. 5). These results provide evidence against a contribution of contaminating LPS in the protection seen with HMGB1 preconditioning.

Example 4

This example demonstrates the use of HMGB1 in treating myocardial infarction.

A patient who has suffered myocardial infarction is administered 15 mg HMGB1 intravenously within 30 minutes after infarction. Conventional treatments for myocardial infarction are also administered, including surgical repair, drug therapy, and/or insertion of a stent.

A patient who is being prepared for a surgical procedure bearing a risk of myocardial infarction is administered 15 mg HMGB1 intravenously one hour prior to surgery. If myocardial infarction occurs during surgery, conventional treatments are administered.

The injury to the treated patients' hearts due to myocardial infarction is decreased compared to the injury to the heart of a control patient treated only with conventional treatments.

Example 5

This example demonstrates the use of HMGB1 in treating ischemic stroke.

A patient who has suffered an ischemic stroke is administered 15 mg HMGB1 intravenously within 30 minutes after the stroke. Conventional treatments for ischemic stroke are also administered.

A patient who is being prepared for a surgical procedure bearing a risk of stroke is administered 15 mg HMGB1 intravenously one hour prior to surgery. If stroke occurs during surgery, conventional treatments are administered.

The injury to treated patients' brains due to stroke is decreased compared to the brain injury of a control patient treated only with conventional treatments.

Example 6

This example demonstrates the use of HMGB1 in treating traumatic injury.

A patient who has suffered a traumatic injury is administered 15 mg of HMGB1 intravenously within 30 minutes after injury. Conventional treatments for the traumatic injury are also administered.

The patient's injury is decreased compared to a control patient treated only with conventional treatments.

Example 7

This example demonstrates the use of HMGB1 in treating hemorrhagic shock.

A patient who is suffering from hemorrhagic shock is administered 15 mg HMGB1 intravenously within 30 minutes after the insult leading to shock occurs. Conventional treatments for hemorrhagic shock are also administered.

A patient who is being prepared for a surgical procedure bearing a risk of extreme blood loss and/or hemorrhagic shock is administered 15 mg HMGB1 intravenously one hour prior to surgery. If hemorrhagic shock occurs during surgery, conventional treatments are administered.

The patient's injury is decreased compared to a control patient treated only with conventional treatments.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments can become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. A method of protecting a heart, liver or a portion of a liver contained within a host animal from injury resulting from controlled ischemia and reperfusion of the heart, liver or a portion of a liver, the method comprising administering to the host animal prior to the initial ischemic insult a mammalian High Mobility Group Box 1 (HMGB1) protein in an amount effective to protect the heart, liver or portion of a liver from injury.

2. The method of claim 1, wherein the HMGB1 protein comprises a polypeptide having the amino acid sequence of SEQ ID NO:2.

3. The method of claim 1, wherein the HMGB1 protein consists of a polypeptide having the amino acid sequence of SEQ ID NO:2.

4. The method of claim 1, wherein the HMGB1 protein is administered about one hour prior to the injury.

5. The method of claim 1, wherein the HMGB1 protein is administered about 45 minutes prior to the injury.

6. The method of claim 1, wherein the HMGB1 protein is administered about 30 minutes prior to the injury.

7. The method of claim 1, wherein the HMGB1 protein is administered about 15 minutes prior to the injury.

8. The method of claim 1, wherein the HMGB1 protein is administered about 10 minutes prior to the injury.

9. The method of claim 1, wherein the HMGB1 protein is administered about 5 minutes prior to the injury.

10. The method of claim 1, wherein the host is a human.

11. The method of claim 1, wherein the host is a non-human mammal.

12. The method of claim 1, wherein the HMGB1 protein is administered systemically to the host.

13. The method of claim 1, wherein the HMGB1 protein is administered by a route selected from the group consisting of intravenous, intramuscular, intraperitoneal, percutaneous, subcutaneous, topical, transmucosal, or oral.

14. The method of claim 1, wherein the HMGB1 protein is administered locally to the heart, liver or a portion of a liver.

15. The method of claim 1, wherein the HMGB1 protein is administered in a dosage of about 5 µg to about 35 mg.

16. The method of claim 15, wherein the HMGB1 protein is administered in a dosage of about 5 µg to about 20 µg.

17. The method of claim 15, wherein the HMGB1 protein is administered in a dosage of about 20 µg to about 1 mg.

18. The method of claim 15, wherein the HMGB1 protein is administered in a dosage of about 1 mg to about 10 mg.

19. The method of claim 15, wherein the HMGB1 protein is administered in a dosage of about 10 mg to about 35 mg.

20. The method of claim 1, wherein the injury resulting from controlled ischemia and reperfusion occurs during transplantation of the heart, liver or portion of a liver from a donor to a recipient, and wherein the HMGB1 protein is administered to the donor prior to the initial ischemic insult.

21. The method of claim 1, wherein the ischemia and reperfusion occur during a surgical procedure.

22. The method of claim 1, wherein the heart, liver or a portion of a liver is a heart.

23. The method of claim 1, wherein the heart, liver or a portion of a liver is a liver or a portion of a liver.

24. The method of claim 1, wherein the host animal is a donor of the heart, liver or portion of the liver.

25. The method of claim 24, wherein the donor is a cadaver donor.

26. The method of claim 24, wherein the donor is a human.

27. The method of claim 24, wherein the donor is a non-human mammal.

28. The method of claim 24, wherein the HMGB1 protein is administered systemically to the donor.

29. The method of claim 1, wherein the HMGB1 protein is administered locally to the heart, liver or portion of the liver.

30. The method of claim 24, wherein the HMGB1 protein is administered by a route selected from the group consisting of intravenous, intramuscular, intraperitoneal, percutaneous, subcutaneous, transmucosal, topical, or oral.

* * * * *

SEQUENCE LISTING

<160> NUMBER OF SEQ ID NOS: 38

<210> SEQ ID NO 1
<211> LENGTH: 215
<212> TYPE: PRT
<213> ORGANISM: Homo sapiens

<400> SEQUENCE: 1

```
Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Glu Asp Glu Glu
            180                 185                 190

Asp Glu Glu Asp Glu Glu Glu Glu Asp Glu Glu Asp Glu Asp Glu
        195                 200                 205

Glu Glu Asp Asp Asp Asp Glu
    210                 215
```

<210> SEQ ID NO 2
<211> LENGTH: 215
<212> TYPE: PRT
<213> ORGANISM: Mus musculus

<400> SEQUENCE: 2

```
Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30
```

```
Asp Ala Ser Val Asn Phe Ser Glu Phe Ser Lys Lys Cys Ser Glu Arg
            35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Asp Glu Glu
            180                 185                 190

Asp Glu Glu Asp Glu Glu Glu Glu Glu Glu Asp Glu Asp
            195                 200                 205

Glu Glu Asp Asp Asp Glu
        210                 215

<210> SEQ ID NO 3
<211> LENGTH: 209
<212> TYPE: PRT
<213> ORGANISM: Homo sapiens

<400> SEQUENCE: 3

Met Gly Lys Gly Asp Pro Asn Lys Pro Arg Gly Lys Met Ser Ser Tyr
1               5                   10                  15

Ala Phe Phe Val Gln Thr Cys Arg Glu Glu His Lys Lys Lys His Pro
                20                  25                  30

Asp Ser Ser Val Asn Phe Ala Glu Phe Ser Lys Lys Cys Ser Glu Arg
            35                  40                  45

Trp Lys Thr Met Ser Ala Lys Glu Lys Ser Lys Phe Glu Asp Met Ala
    50                  55                  60

Lys Ser Asp Lys Ala Arg Tyr Asp Arg Glu Met Lys Asn Tyr Val Pro
65                  70                  75                  80

Pro Lys Gly Asp Lys Lys Gly Lys Lys Asp Pro Asn Ala Pro Lys
                85                  90                  95

Arg Pro Pro Ser Ala Phe Phe Leu Phe Cys Ser Glu His Arg Pro Lys
            100                 105                 110

Ile Lys Ser Glu His Pro Gly Leu Ser Ile Gly Asp Thr Ala Lys Lys
        115                 120                 125

Leu Gly Glu Met Trp Ser Glu Gln Ser Ala Lys Asp Lys Gln Pro Tyr
    130                 135                 140

Glu Gln Lys Ala Ala Lys Leu Lys Glu Lys Tyr Glu Lys Asp Ile Ala
145                 150                 155                 160

Ala Tyr Arg Ala Lys Gly Lys Ser Glu Ala Gly Lys Lys Gly Pro Gly
                165                 170                 175

Arg Pro Thr Gly Ser Lys Lys Lys Asn Glu Pro Glu Asp Glu Glu Glu
```

-continued

```
                    180                 185                 190
Glu Glu Glu Glu Glu Asp Glu Asp Glu Glu Glu Asp Glu Asp Glu
                195                 200                 205

Glu

<210> SEQ ID NO 4
<211> LENGTH: 54
<212> TYPE: PRT
<213> ORGANISM: Homo sapiens

<400> SEQUENCE: 4

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
                20                  25                  30

Ala Lys Ala Asp Lys Ala Arg Tyr Glu Arg Glu Met Lys Thr Tyr Ile
            35                  40                  45

Pro Pro Lys Gly Glu Thr
        50

<210> SEQ ID NO 5
<211> LENGTH: 69
<212> TYPE: PRT
<213> ORGANISM: Homo sapiens

<400> SEQUENCE: 5

Asn Ala Pro Lys Arg Pro Pro Ser Ala Phe Phe Leu Phe Cys Ser Glu
1               5                   10                  15

Tyr Arg Pro Lys Ile Lys Gly Glu His Pro Gly Leu Ser Ile Gly Asp
                20                  25                  30

Val Ala Lys Lys Leu Gly Glu Met Trp Asn Asn Thr Ala Ala Asp Asp
            35                  40                  45

Lys Gln Pro Tyr Glu Lys Lys Ala Ala Lys Leu Lys Glu Lys Tyr Glu
        50                  55                  60

Lys Asp Ile Ala Ala
65

<210> SEQ ID NO 6
<211> LENGTH: 22
<212> TYPE: DNA
<213> ORGANISM: Homo sapiens

<400> SEQUENCE: 6
gatgggcaaa ggagatccta ag                                         22

<210> SEQ ID NO 7
<211> LENGTH: 29
<212> TYPE: DNA
<213> ORGANISM: Homo sapiens

<400> SEQUENCE: 7
gcggccgctt attcatcatc atcatcttc                                  29

<210> SEQ ID NO 8
<211> LENGTH: 22
<212> TYPE: DNA
<213> ORGANISM: Homo sapiens

<400> SEQUENCE: 8
gatgggcaaa ggagatccta ag                                         22
```

<210> SEQ ID NO 9
<211> LENGTH: 32
<212> TYPE: DNA
<213> ORGANISM: Homo sapiens

<400> SEQUENCE: 9
gcggccgctc acttgctttt ttcagccttg ac                          32

<210> SEQ ID NO 10
<211> LENGTH: 21
<212> TYPE: DNA
<213> ORGANISM: Homo sapiens

<400> SEQUENCE: 10
gagcataaga agaagcaccc a                                      21

<210> SEQ ID NO 11
<211> LENGTH: 32
<212> TYPE: DNA
<213> ORGANISM: Homo sapiens

<400> SEQUENCE: 11
gcggccgctc acttgctttt ttcagccttg ac                          32

<210> SEQ ID NO 12
<211> LENGTH: 24
<212> TYPE: DNA
<213> ORGANISM: Homo sapiens

<400> SEQUENCE: 12
aagttcaagg atcccaatgc aaag                                   24

<210> SEQ ID NO 13
<211> LENGTH: 32
<212> TYPE: DNA
<213> ORGANISM: Homo sapiens

<400> SEQUENCE: 13
gcggccgctc aatatgcagc tatatccttt tc                          32

<210> SEQ ID NO 14
<211> LENGTH: 22
<212> TYPE: DNA
<213> ORGANISM: Homo sapiens

<400> SEQUENCE: 14
gatgggcaaa ggagatccta ag                                     22

<210> SEQ ID NO 15
<211> LENGTH: 24
<212> TYPE: DNA
<213> ORGANISM: Homo sapiens

<400> SEQUENCE: 15 tcacttttt gtctcccctt tggg                                    24

<210> SEQ ID NO 16
<211> LENGTH: 20
<212> TYPE: PRT
<213> ORGANISM: Homo sapiens

<400> SEQUENCE: 16

```
Phe Lys Asp Pro Asn Ala Pro Lys Arg Leu Pro Ser Ala Phe Phe Leu
1               5                   10                  15

Phe Cys Ser Glu
            20
```

<210> SEQ ID NO 17
<211> LENGTH: 54
<212> TYPE: PRT
<213> ORGANISM: Homo sapiens

<400> SEQUENCE: 17

```
Pro Asp Ser Ser Val Asn Phe Ala Glu Phe Ser Lys Lys Cys Ser Glu
1               5                   10                  15

Arg Trp Lys Thr Met Ser Ala Lys Glu Lys Ser Lys Phe Glu Asp Met
            20                  25                  30

Ala Lys Ser Asp Lys Ala Arg Tyr Asp Arg Glu Met Lys Asn Tyr Val
        35                  40                  45

Pro Pro Lys Gly Asp Lys
    50
```

<210> SEQ ID NO 18
<211> LENGTH: 216
<212> TYPE: PRT
<213> ORGANISM: Homo sapiens

<400> SEQUENCE: 18

```
Met Gly Lys Gly Asp Pro Lys Lys Pro Thr Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Leu Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
            115                 120                 125

Leu Gly Glu Met Trp Asn Asn Thr Ala Ala Asp Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys Lys Lys Glu Glu Glu Asp Glu Glu
            180                 185                 190

Asp Glu Glu Asp Glu Glu Glu Glu Asp Glu Glu Asp Glu Glu Glu Asp
        195                 200                 205

Glu Glu Glu Asp Asp Asp Glu
        210                 215
```

<210> SEQ ID NO 19
<211> LENGTH: 182

```
<212> TYPE: PRT
<213> ORGANISM: Homo sapiens

<400> SEQUENCE: 19

Met Gly Lys Gly Asp Pro Lys Lys Pro Thr Gly Lys Met Ser Ser Tyr
1               5                   10                  15

Ala Phe Phe Val Gln Thr Cys Arg Glu Glu His Lys Lys Lys His Pro
                20                  25                  30

Asp Ala Ser Val Asn Phe Ser Glu Phe Ser Lys Lys Cys Ser Glu Arg
            35                  40                  45

Trp Lys Thr Met Ser Ala Lys Glu Lys Gly Lys Phe Glu Asp Met Ala
50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Leu Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Asp Lys Gln Pro Tyr
130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp Ala Ala Lys Lys Gly Val Val
                165                 170                 175

Lys Ala Glu Lys Ser Lys
            180

<210> SEQ ID NO 20
<211> LENGTH: 74
<212> TYPE: PRT
<213> ORGANISM: Homo sapiens

<400> SEQUENCE: 20

Phe Lys Asp Pro Asn Ala Pro Lys Arg Leu Pro Ser Ala Phe Phe Leu
1               5                   10                  15

Phe Cys Ser Glu Tyr Arg Pro Lys Ile Lys Gly Glu His Pro Gly Leu
                20                  25                  30

Ser Ile Gly Asp Val Ala Lys Lys Leu Gly Glu Met Trp Asn Asn Thr
            35                  40                  45

Ala Ala Asp Asp Lys Gln Pro Tyr Glu Lys Lys Ala Ala Lys Leu Lys
    50                  55                  60

Glu Lys Tyr Glu Lys Asp Ile Ala Ala Tyr
65                  70

<210> SEQ ID NO 21
<211> LENGTH: 85
<212> TYPE: PRT
<213> ORGANISM: Homo sapiens

<400> SEQUENCE: 21

Met Gly Lys Gly Asp Pro Lys Lys Pro Thr Gly Lys Met Ser Ser Tyr
1               5                   10                  15

Ala Phe Phe Val Gln Thr Cys Arg Glu Glu His Lys Lys Lys His Pro
                20                  25                  30

Asp Ala Ser Val Asn Phe Ser Glu Phe Ser Lys Lys Cys Ser Glu Arg
```

```
                35                  40                  45
Trp Lys Thr Met Ser Ala Lys Glu Lys Gly Lys Phe Glu Asp Met Ala
 50                  55                  60

Lys Ala Asp Lys Ala Arg Tyr Glu Arg Glu Met Lys Thr Tyr Ile Pro
 65                  70                  75                  80

Pro Lys Gly Glu Thr
                 85

<210> SEQ ID NO 22
<211> LENGTH: 77
<212> TYPE: PRT
<213> ORGANISM: Homo sapiens

<400> SEQUENCE: 22

Pro Thr Gly Lys Met Ser Ser Tyr Ala Phe Phe Val Gln Thr Cys Arg
  1               5                  10                  15

Glu Glu His Lys Lys Lys His Pro Asp Ala Ser Val Asn Phe Ser Glu
                 20                  25                  30

Phe Ser Lys Lys Cys Ser Glu Arg Trp Lys Thr Met Ser Ala Lys Glu
             35                  40                  45

Lys Gly Lys Phe Glu Asp Met Ala Lys Ala Asp Lys Ala Arg Tyr Glu
 50                  55                  60

Arg Glu Met Lys Thr Tyr Ile Pro Pro Lys Gly Glu Thr
 65                  70                  75

<210> SEQ ID NO 23
<211> LENGTH: 20
<212> TYPE: PRT
<213> ORGANISM: Homo sapiens

<400> SEQUENCE: 23

Asn Ala Pro Lys Arg Pro Pro Ser Ala Phe Phe Leu Phe Cys Ser Glu
  1               5                  10                  15

Tyr Arg Pro Lys
             20

<210> SEQ ID NO 24
<211> LENGTH: 169
<212> TYPE: PRT
<213> ORGANISM: Mus musculus

<400> SEQUENCE: 24

Met Gly Lys Gly Asp Pro Lys Lys Pro Arg Gly Lys Met Ser Ser Tyr
  1               5                  10                  15

Ala Phe Phe Val Gln Thr Cys Arg Glu Glu His Lys Lys Lys His Pro
                 20                  25                  30

Asp Ala Ser Val Asn Phe Ser Glu Phe Ser Lys Lys Cys Ser Glu Arg
             35                  40                  45

Trp Lys Thr Met Ser Ala Lys Glu Lys Gly Lys Phe Glu Asp Met Ala
 50                  55                  60

Lys Ala Asp Lys Ala Arg Tyr Glu Arg Glu Met Lys Thr Tyr Ile Pro
 65                  70                  75                  80

Pro Lys Gly Glu Thr Lys Lys Lys Phe Lys Asp Pro Asn Ala Pro Lys
                 85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
            115                 120                 125
```

```
Leu Gly Glu Met Trp Asn Asn Thr Ala Ala Asp Asp Lys Gln Pro Tyr
        130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp
                165

<210> SEQ ID NO 25
<211> LENGTH: 54
<212> TYPE: PRT
<213> ORGANISM: Synthetic construct

<400> SEQUENCE: 25

Pro Asp Ala Ser Val Asn Phe Ser Glu Phe Ser Lys Lys Cys Ser Glu
1               5                   10                  15

Arg Trp Lys Thr Met Ser Ala Lys Glu Lys Gly Lys Phe Glu Asp Met
            20                  25                  30

Ala Lys Ala Asp Lys Ala Arg Tyr Glu Arg Glu Met Lys Thr Tyr Ile
        35                  40                  45

Pro Pro Lys Gly Glu Thr
    50

<210> SEQ ID NO 26
<211> LENGTH: 69
<212> TYPE: PRT
<213> ORGANISM: Synthetic construct

<400> SEQUENCE: 26

Asn Ala Pro Lys Arg Pro Pro Ser Ala Phe Phe Leu Phe Cys Ser Glu
1               5                   10                  15

Tyr Arg Pro Lys Ile Lys Gly Glu His Pro Gly Leu Ser Ile Gly Asp
            20                  25                  30

Val Ala Lys Lys Leu Gly Glu Met Trp Asn Asn Thr Ala Ala Asp Asp
        35                  40                  45

Lys Gln Pro Tyr Glu Lys Lys Ala Ala Lys Leu Lys Glu Lys Tyr Glu
    50                  55                  60

Lys Asp Ile Ala Ala
65

<210> SEQ ID NO 27
<211> LENGTH: 169
<212> TYPE: PRT
<213> ORGANISM: Synthetic construct

<400> SEQUENCE: 27

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95
```

```
Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp
                165

<210> SEQ ID NO 28
<211> LENGTH: 169
<212> TYPE: PRT
<213> ORGANISM: Spalax ehrenbergi

<400> SEQUENCE: 28

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Glu Arg Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp
                165

<210> SEQ ID NO 29
<211> LENGTH: 169
<212> TYPE: PRT
<213> ORGANISM: Pan troglodytes

<400> SEQUENCE: 29

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80
```

```
Pro Lys Glu Glu Thr Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
                100                 105                 110

Ile Lys Gly Glu His Pro Gly Leu Ser Val Gly Asp Val Ala Lys Lys
                115                 120                 125

Leu Gly Glu Met Trp Asn Asn Ala Ala Ala Asp Asp Lys Gln Pro Tyr
            130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp
                165

<210> SEQ ID NO 30
<211> LENGTH: 169
<212> TYPE: PRT
<213> ORGANISM: Mus musculus

<400> SEQUENCE: 30

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Arg Lys His Pro
                20                  25                  30

Asp Ala Ser Val Asn Phe Ser Glu Phe Ser Lys Lys Cys Ser Glu Arg
            35                  40                  45

Trp Lys Thr Met Ser Ala Lys Glu Lys Gly Lys Phe Glu Asp Met Ala
    50                  55                  60

Lys Ala Asp Lys Ala Arg Tyr Glu Arg Glu Met Lys Thr Tyr Ile Pro
65                  70                  75                  80

Pro Lys Gly Glu Thr Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
                100                 105                 110

Ile Lys Gly Glu His Pro Gly Leu Ser Ile Gly Asp Val Ala Lys Lys
                115                 120                 125

Leu Gly Glu Met Trp Asn Asn Thr Ala Ala Asp Asp Lys Gln Pro Tyr
            130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp
                165

<210> SEQ ID NO 31
<211> LENGTH: 169
<212> TYPE: PRT
<213> ORGANISM: Homo sapiens

<400> SEQUENCE: 31

Met Gly Lys Gly Asp Pro Lys Lys Pro Arg Gly Lys Met Ser Ser Tyr
1               5                   10                  15

Ala Phe Phe Val Gln Thr Cys Arg Glu Glu His Lys Lys Lys His Pro
                20                  25                  30

Asp Ala Ser Val Asn Phe Ser Glu Phe Ser Lys Lys Cys Ser Glu Arg
            35                  40                  45

Trp Lys Thr Met Ser Ala Lys Glu Lys Gly Lys Phe Glu Asp Met Ala
    50                  55                  60
```

```
Lys Ala Asp Lys Ala Arg Tyr Glu Arg Glu Met Lys Thr Tyr Ile Pro
 65                  70                  75                  80

Pro Lys Gly Glu Thr Lys Lys Phe Lys Asp Pro Asn Ala Pro Lys
                 85                  90                  95

Arg Pro Pro Ser Ala Phe Phe Leu Phe Cys Ser Glu Tyr Arg Pro Lys
                100                 105                 110

Ile Lys Gly Glu His Pro Gly Leu Ser Ile Gly Asp Val Ala Lys Lys
            115                 120                 125

Leu Gly Glu Met Trp Asn Asn Thr Ala Ala Asp Asp Lys Gln Pro Tyr
        130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp
                165
```

<210> SEQ ID NO 32
<211> LENGTH: 169
<212> TYPE: PRT
<213> ORGANISM: Mus musculus

<400> SEQUENCE: 32

```
Met Gly Lys Gly Asp Pro Lys Lys Pro Arg Gly Lys Met Ser Ser Tyr
 1               5                  10                  15

Ala Phe Phe Val Gln Thr Cys Arg Glu Glu His Lys Lys Lys His Pro
                 20                  25                  30

Asp Ala Ser Val Asn Phe Ser Glu Phe Ser Lys Lys Cys Ser Glu Arg
            35                  40                  45

Trp Lys Thr Met Ser Ala Lys Glu Lys Gly Lys Phe Glu Asp Met Ala
 50                  55                  60

Lys Ala Asp Lys Ala Arg Tyr Glu Arg Glu Met Lys Thr Tyr Ile Pro
 65                  70                  75                  80

Pro Lys Gly Glu Thr Lys Lys Phe Lys Asp Pro Asn Ala Pro Lys
                 85                  90                  95

Arg Pro Pro Ser Ala Phe Phe Leu Phe Cys Ser Glu Tyr Arg Pro Lys
                100                 105                 110

Ile Lys Gly Glu His Pro Gly Leu Ser Ile Gly Asp Val Ala Lys Lys
            115                 120                 125

Leu Gly Glu Met Trp Asn Asn Thr Ala Ala Asp Asp Lys Gln Pro Tyr
        130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp
                165
```

<210> SEQ ID NO 33
<211> LENGTH: 169
<212> TYPE: PRT
<213> ORGANISM: Homo sapiens

<400> SEQUENCE: 33

```
Met Gly Lys Gly Asp Pro Lys Lys Pro Arg Gly Lys Met Ser Ser Tyr
 1               5                  10                  15

Ala Phe Phe Val Gln Thr Cys Arg Glu Glu His Lys Lys Lys His Pro
                 20                  25                  30

Asp Ala Ser Val Asn Phe Ser Glu Phe Ser Lys Lys Cys Ser Glu Arg
            35                  40                  45
```

```
Trp Lys Thr Met Ser Ala Lys Glu Lys Gly Lys Phe Glu Asp Met Ala
        50                  55                  60

Lys Ala Asp Lys Ala Arg Tyr Glu Arg Glu Met Lys Thr Tyr Ile Pro
 65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp
                165

<210> SEQ ID NO 34
<211> LENGTH: 169
<212> TYPE: PRT
<213> ORGANISM: Bos taurus

<400> SEQUENCE: 34

Met Gly Lys Gly Asp Pro Lys Lys Pro Arg Gly Lys Met Ser Ser Tyr
 1               5                  10                  15

Ala Phe Phe Val Gln Thr Cys Arg Glu Glu His Lys Lys Lys His Pro
                20                  25                  30

Asp Ala Ser Val Asn Phe Ser Glu Phe Ser Lys Lys Cys Ser Glu Arg
            35                  40                  45

Trp Lys Thr Met Ser Ala Lys Glu Lys Gly Lys Phe Glu Asp Met Ala
        50                  55                  60

Lys Ala Asp Lys Ala Arg Tyr Glu Arg Glu Met Lys Thr Tyr Ile Pro
 65                  70                  75                  80

Pro Lys Gly Glu Thr Lys Lys Lys Phe Lys Asp Pro Asn Ala Pro Lys
                85                  90                  95

Arg Pro Pro Ser Ala Phe Phe Leu Phe Cys Ser Glu Tyr Arg Pro Lys
            100                 105                 110

Ile Lys Gly Glu His Pro Gly Leu Ser Ile Gly Asp Val Ala Lys Lys
        115                 120                 125

Leu Gly Glu Met Trp Asn Asn Thr Ala Ala Asp Lys Gln Pro Tyr
    130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp
                165

<210> SEQ ID NO 35
<211> LENGTH: 169
<212> TYPE: PRT
<213> ORGANISM: Sus scrofa

<400> SEQUENCE: 35

Met Gly Lys Gly Asp Pro Lys Lys Pro Arg Gly Lys Met Ser Ser Tyr
 1               5                  10                  15

Ala Phe Phe Val Gln Thr Cys Arg Glu Glu His Lys Lys Lys His Pro
                20                  25                  30
```

```
Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
 50                  55                  60

Lys Ala Asp Lys Ala Arg Tyr Glu Arg Glu Met Lys Thr Tyr Ile Pro
 65                  70                  75                  80

Pro Lys Gly Glu Thr Lys Lys Lys Phe Lys Asp Pro Asn Ala Pro Lys
                 85                  90                  95

Arg Pro Pro Ser Ala Phe Phe Leu Phe Cys Ser Glu Tyr Arg Pro Lys
                100                 105                 110

Ile Lys Gly Glu His Pro Gly Leu Ser Ile Gly Asp Val Ala Lys Lys
                115                 120                 125

Leu Gly Glu Met Trp Asn Asn Thr Ala Ala Asp Asp Lys Gln Pro Tyr
                130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp
                165

<210> SEQ ID NO 36
<211> LENGTH: 169
<212> TYPE: PRT
<213> ORGANISM: Mus musculus

<400> SEQUENCE: 36

Met Gly Lys Gly Asp Pro Lys Lys Pro Arg Gly Lys Met Ser Ser Tyr
 1               5                  10                  15

Ala Phe Phe Val Gln Thr Cys Arg Glu Glu His Lys Lys Lys His Pro
                 20                  25                  30

Asp Ala Ser Val Asn Phe Ser Glu Phe Ser Lys Lys Cys Ser Glu Arg
        35                  40                  45

Trp Lys Thr Met Ser Ala Lys Glu Lys Gly Lys Phe Glu Asp Met Ala
 50                  55                  60

Lys Ala Asp Lys Ala Arg Tyr Glu Arg Glu Met Lys Thr Tyr Ile Pro
 65                  70                  75                  80

Thr Lys Gly Glu Thr Lys Lys Lys Phe Lys Asp Pro Asn Ala Pro Lys
                 85                  90                  95

Arg Pro Pro Ser Ala Phe Phe Leu Phe Cys Ser Glu Tyr Arg Pro Lys
                100                 105                 110

Ile Lys Gly Glu His Pro Gly Leu Ser Ile Gly Asp Val Ala Lys Lys
                115                 120                 125

Leu Gly Glu Met Trp Asn Asn Thr Ala Ala Asp Asp Lys Gln Pro Tyr
                130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Pro Asp
                165

<210> SEQ ID NO 37
<211> LENGTH: 169
<212> TYPE: PRT
<213> ORGANISM: Gallus gallus

<400> SEQUENCE: 37

Met Gly Lys Gly Asp Pro Lys Lys Pro Arg Gly Lys Met Ser Ser Tyr
 1               5                  10                  15
```

```
Ala Phe Phe Val Gln Thr Cys Arg Glu Glu His Lys Lys His Pro
            20                  25                  30

Asp Ala Ser Val Asn Phe Ser Glu Phe Ser Lys Lys Cys Ser Glu Arg
        35                  40                  45

Trp Lys Thr Met Ser Ser Lys Glu Lys Gly Lys Phe Glu Asp Met Ala
    50                  55                  60

Lys Ala Asp Lys Leu Arg Tyr Glu Lys Glu Met Lys Asn Tyr Val Pro
65                  70                  75                  80

Pro Lys Gly Glu Thr Lys Lys Phe Lys Asp Pro Asn Ala Pro Lys
                85                  90                  95

Arg Pro Pro Ser Ala Phe Phe Leu Phe Cys Ser Glu Phe Arg Pro Lys
                100                 105                 110

Ile Lys Gly Glu His Pro Gly Leu Ser Ile Gly Asp Val Ala Lys Lys
            115                 120                 125

Leu Gly Glu Met Trp Asn Asn Thr Ala Ala Asp Lys Gln Pro Tyr
                130                 135                 140

Glu Lys Lys Ala Ala Lys Leu Lys Glu Lys Tyr Glu Lys Asp Ile Ala
145                 150                 155                 160

Ala Tyr Arg Ala Lys Gly Lys Val Asp
                165

<210> SEQ ID NO 38
<211> LENGTH: 169
<212> TYPE: PRT
<213> ORGANISM: Xenopus tropicalis

<400> SEQUENCE: 38

Met Gly Lys Gly Asp Pro Lys Lys Pro Arg Gly Lys Met Ser Ser Tyr
1               5                   10                  15

Ala Tyr Phe Val Gln Thr Cys Arg Glu Glu His Lys Lys Lys His Pro
            20                  25                  30

Asp Ala Ser Val Asn Phe Ala Glu Phe Ser Lys Lys Cys Ser Glu Arg
        35                  40                  45

Trp Lys Thr Met Ser Ala Lys Glu Lys Ser Lys Phe Glu Asp Met Ala
    50                  55                  60

Lys Ala Asp Lys Val Arg Tyr Glu Arg Glu Met Lys Thr Tyr Ile Pro
65                  70                  75                  80

Pro Lys Gly Glu Thr Lys Lys Phe Lys Asp Pro Asn Ala Pro Lys
                85                  90                  95

Arg Pro Pro Ser Ala Phe Phe Leu Phe Cys Ser Glu Phe Arg Pro Lys
                100                 105                 110

Ile Lys Gly Glu His Pro Gly Ser Thr Ile Gly Asp Ile Ala Lys Lys
            115                 120                 125

Leu Gly Glu Met Trp Asn Asn Thr Ala Thr Asp Lys Leu Pro Tyr
                130                 135                 140

Glu Arg Lys Ala Ala Lys Leu Lys Glu Lys Tyr Glu Lys Asp Val Ala
145                 150                 155                 160

Ala Tyr Arg Ala Lys Gly Lys Pro Glu
                165
```